(12) United States Patent
Ballakur et al.

(10) Patent No.: US 9,345,530 B2
(45) Date of Patent: May 24, 2016

(54) DEVICES, SYSTEMS AND METHODS FOR EVALUATION AND FEEDBACK OF NEUROMODULATION TREATMENT

(71) Applicant: Medtronic Ardian Luxembourg S.a.r.l., Luxembourg (LU)

(72) Inventors: Sowmya Ballakur, Ithaca, NY (US); Robert J. Beetel, Woodside, CA (US); Paul Friedrichs, Belmont, CA (US); David Herzfeld, Grafton, WI (US); Andrew Wu, Los Altos Hills, CA (US); Denise Zarins, Saratoga, CA (US); Mark S. Leung, Duncan (CA)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 14/718,843

(22) Filed: May 21, 2015

(65) Prior Publication Data
US 2015/0257815 A1    Sep. 17, 2015

Related U.S. Application Data

(63) Continuation of application No. 13/281,269, filed on Oct. 25, 2011, now Pat. No. 9,066,720.

(60) Provisional application No. 61/406,531, filed on Oct. 25, 2010, provisional application No. 61/528,108, filed on Aug. 26, 2011, provisional application No. 61/528,091, filed on Aug. 26, 2011, provisional application No. 61/528,684, filed on Aug. 29, 2011.

(51) Int. Cl.
*A61B 18/12* (2006.01)
*A61B 18/10* (2006.01)
(Continued)

(52) U.S. Cl.
CPC ............. *A61B 18/1206* (2013.01); *A61B 18/10* (2013.01); *A61F 7/12* (2013.01);
(Continued)

(58) Field of Classification Search
CPC ............... A61B 18/10; A61B 18/1206; A61B 18/1492; A61B 2017/00075; A61B 2018/00404; A61B 2018/00511; A61B 2018/00577; A61B 2018/00642; A61B 2018/00648; A61B 2018/00672; A61B 2018/00678; A61B 2018/00702; A61B 2018/00761; A61B 2018/00791; A61B 2018/00797; A61B 2018/00815; A61B 2018/00821; A61B 2018/00863; A61B 2018/00875; A61B 2018/00434
See application file for complete search history.

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| EP | 0768841 | 4/1997 |
| EP | 1169976 | 1/2002 |

(Continued)

OTHER PUBLICATIONS

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

(Continued)

*Primary Examiner* — Amanda Patton

(57) ABSTRACT

The present disclosure relates to devices, systems and methods for evaluating the success of a treatment applied to tissue in a patient, such as a radio frequency ablative treatment used to neuromodulate nerves associated with the renal artery. A system monitors parameters or values generated during the course of a treatment. Feedback provided to an operator is based on the monitored values and relates to an assessment of the likelihood that a completed treatment was technically successful. In other embodiments, parameters or values generated during the course of an incomplete treatment (such as due to high temperature or high impedance conditions) may be evaluated to provide additional instructions or feedback to an operator.

18 Claims, 14 Drawing Sheets

(51) Int. Cl.
*A61F 7/12* (2006.01)
*A61B 18/14* (2006.01)
*A61B 17/00* (2006.01)
*A61B 18/00* (2006.01)
*A61F 7/00* (2006.01)

(52) U.S. Cl.
CPC .. *A61B 18/1492* (2013.01); *A61B 2017/00075* (2013.01); *A61B 2018/00404* (2013.01); *A61B 2018/00434* (2013.01); *A61B 2018/00505* (2013.01); *A61B 2018/00511* (2013.01); *A61B 2018/00577* (2013.01); *A61B 2018/00642* (2013.01); *A61B 2018/00648* (2013.01); *A61B 2018/00672* (2013.01); *A61B 2018/00678* (2013.01); *A61B 2018/00702* (2013.01); *A61B 2018/00761* (2013.01); *A61B 2018/00791* (2013.01); *A61B 2018/00797* (2013.01); *A61B 2018/00815* (2013.01); *A61B 2018/00821* (2013.01); *A61B 2018/00863* (2013.01); *A61B 2018/00875* (2013.01); *A61F 2007/0093* (2013.01)

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,301,683 A | 4/1994 | Durkan |
| 5,358,514 A | 10/1994 | Schulman et al. |
| 5,368,591 A | 11/1994 | Lennox et al. |
| 5,423,744 A | 6/1995 | Gencheff et al. |
| 5,423,808 A | 6/1995 | Edwards et al. |
| 5,423,810 A | 6/1995 | Goble et al. |
| 5,425,364 A | 6/1995 | Imran |
| 5,437,662 A | 8/1995 | Nardella |
| 5,437,664 A | 8/1995 | Cohen et al. |
| 5,472,443 A | 12/1995 | Cordis et al. |
| 5,484,400 A | 1/1996 | Edwards et al. |
| 5,496,312 A | 3/1996 | Klicek |
| 5,540,681 A | 7/1996 | Strul et al. |
| 5,540,684 A | 7/1996 | Hassler, Jr. |
| 5,562,721 A | 10/1996 | Marchlinski et al. |
| 5,571,147 A | 11/1996 | Sluijter et al. |
| 5,573,533 A | 11/1996 | Strul |
| 5,584,830 A | 12/1996 | Ladd et al. |
| 5,588,964 A | 12/1996 | Imran et al. |
| 5,599,345 A | 2/1997 | Edwards et al. |
| 5,626,576 A | 5/1997 | Janssen |
| 5,658,619 A | 8/1997 | Kirschner et al. |
| 5,672,174 A | 9/1997 | Gough et al. |
| 5,688,266 A | 11/1997 | Edwards et al. |
| 5,697,882 A | 12/1997 | Eggers et al. |
| 5,697,925 A | 12/1997 | Taylor |
| 5,700,282 A | 12/1997 | Zabara |
| 5,702,386 A | 12/1997 | Stern et al. |
| 5,707,400 A | 1/1998 | Terry, Jr. et al. |
| 5,735,846 A | 4/1998 | Panescu et al. |
| 5,755,715 A | 5/1998 | Stern et al. |
| 5,769,847 A | 6/1998 | Panescu et al. |
| 5,772,590 A | 6/1998 | Webster, Jr. |
| 5,810,802 A | 9/1998 | Panescu et al. |
| 5,817,092 A | 10/1998 | Behl |
| 5,817,093 A | 10/1998 | Williamson, IV et al. |
| 5,860,974 A | 1/1999 | Abele |
| 5,865,787 A | 2/1999 | Shapland et al. |
| 5,868,737 A | 2/1999 | Taylor et al. |
| 5,871,481 A | 2/1999 | Kannenberg et al. |
| 5,893,885 A | 4/1999 | Webster et al. |
| 5,906,614 A | 5/1999 | Stern et al. |
| 5,907,589 A | 5/1999 | Koifman et al. |
| 5,944,710 A | 8/1999 | Dev et al. |
| 5,954,719 A | 9/1999 | Chen et al. |
| 5,976,128 A | 11/1999 | Schilling et al. |
| 5,983,141 A | 11/1999 | Sluijter et al. |
| 6,004,269 A | 12/1999 | Crowley et al. |
| 6,009,877 A | 1/2000 | Edwards |
| 6,023,638 A | 2/2000 | Swanson |
| 6,024,740 A | 2/2000 | Lesh et al. |
| 6,036,687 A | 3/2000 | Laufer et al. |
| 6,039,731 A | 3/2000 | Taylor et al. |
| 6,066,134 A | 5/2000 | Eggers et al. |
| 6,080,149 A | 6/2000 | Huang et al. |
| 6,091,995 A | 7/2000 | Ingle et al. |
| 6,099,524 A | 8/2000 | Lipson et al. |
| 6,113,592 A | 9/2000 | Taylor |
| 6,117,101 A | 9/2000 | Diederich et al. |
| 6,123,702 A | 9/2000 | Swanson et al. |
| 6,135,999 A | 10/2000 | Fanton et al. |
| 6,149,620 A | 11/2000 | Baker et al. |
| 6,161,048 A | 12/2000 | Sluijter et al. |
| 6,183,468 B1 | 2/2001 | Swanson et al. |
| 6,197,021 B1 | 3/2001 | Panescu et al. |
| 6,210,403 B1 | 4/2001 | Klicek |
| 6,212,426 B1 | 4/2001 | Swanson |
| 6,217,573 B1 | 4/2001 | Webster |
| 6,219,577 B1 | 4/2001 | Brown, III et al. |
| 6,224,592 B1 | 5/2001 | Eggers et al. |
| 6,238,387 B1 | 5/2001 | Miller, III |
| 6,245,065 B1 | 6/2001 | Panescu et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,293,941 B1 | 9/2001 | Strul et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,358,246 B1 | 3/2002 | Behl et al. |
| 6,405,732 B1 | 6/2002 | Edwards et al. |
| 6,413,255 B1 | 7/2002 | Stern |
| 6,423,057 B1 | 7/2002 | He et al. |
| 6,428,537 B1 | 8/2002 | Swanson et al. |
| 6,451,015 B1 | 9/2002 | Rittman, III et al. |
| 6,464,696 B1 | 10/2002 | Oyama et al. |
| 6,488,678 B2 | 12/2002 | Sherman |
| 6,488,679 B1 | 12/2002 | Swanson et al. |
| 6,494,880 B1 | 12/2002 | Swanson et al. |
| 6,500,172 B1 | 12/2002 | Panescu et al. |
| 6,506,189 B1 | 1/2003 | Rittman, III et al. |
| 6,508,815 B1 | 1/2003 | Strul et al. |
| 6,511,476 B2 | 1/2003 | Hareyama |
| 6,514,226 B1 | 2/2003 | Levin et al. |
| 6,514,248 B1 | 2/2003 | Eggers et al. |
| 6,522,926 B1 | 2/2003 | Kieval et al. |
| 6,542,781 B1 | 4/2003 | Koblish et al. |
| 6,546,270 B1 | 4/2003 | Goldin et al. |
| 6,558,378 B2 | 5/2003 | Sherman et al. |
| 6,558,382 B2 | 5/2003 | Jahns et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,635,057 B2 | 10/2003 | Harano et al. |
| 6,648,883 B2 | 11/2003 | Francischelli et al. |
| 6,666,862 B2 | 12/2003 | Jain et al. |
| 6,679,269 B2 | 1/2004 | Swanson |
| 6,682,527 B2 | 1/2004 | Strul |
| 6,685,648 B2 | 2/2004 | Flaherty et al. |
| 6,685,700 B2 | 2/2004 | Behl et al. |
| 6,711,444 B2 | 3/2004 | Koblish |
| 6,730,079 B2 | 5/2004 | Lovewell |
| 6,733,498 B2 | 5/2004 | Paton et al. |
| 6,736,835 B2 | 5/2004 | Pellegrino et al. |
| 6,752,804 B2 | 6/2004 | Simpson et al. |
| 6,752,805 B2 | 6/2004 | Maguire et al. |
| 6,761,716 B2 | 7/2004 | Kadhiresan et al. |
| 6,796,981 B2 | 9/2004 | Wham et al. |
| 6,845,267 B2 | 1/2005 | Harrison et al. |
| 6,849,073 B2 | 2/2005 | Hoey et al. |

(56) References Cited

U.S. PATENT DOCUMENTS

| | | |
|---|---|---|
| 6,850,801 B2 | 2/2005 | Kieval et al. |
| 6,855,141 B2 | 2/2005 | Lovewell |
| 6,855,142 B2 | 2/2005 | Harano et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,936,047 B2 | 8/2005 | Nasab et al. |
| 6,939,346 B2 | 9/2005 | Kannenberg et al. |
| 6,955,675 B2 | 10/2005 | Jain |
| 6,989,010 B2 | 1/2006 | Francischelli et al. |
| 7,001,379 B2 | 2/2006 | Behl et al. |
| 7,001,381 B2 | 2/2006 | Harano et al. |
| 7,008,417 B2 | 3/2006 | Eick |
| 7,025,764 B2 | 4/2006 | Paton et al. |
| 7,029,470 B2 | 4/2006 | Francischelli et al. |
| 7,066,933 B2 | 6/2006 | Hagg |
| 7,076,399 B2 | 7/2006 | Godara |
| 7,104,985 B2 | 9/2006 | Martinelli |
| 7,108,694 B2 | 9/2006 | Miura et al. |
| 7,131,445 B2 | 11/2006 | Amoah |
| 7,137,980 B2 | 11/2006 | Buysse et al. |
| 7,149,574 B2 | 12/2006 | Yun et al. |
| 7,160,296 B2 | 1/2007 | Pearson et al. |
| 7,162,303 B2 | 1/2007 | Levin et al. |
| 7,169,144 B2 | 1/2007 | Hoey et al. |
| 7,221,979 B2 | 5/2007 | Zhou et al. |
| 7,226,447 B2 | 6/2007 | Uchida et al. |
| 7,247,155 B2 | 7/2007 | Hoey et al. |
| 7,250,048 B2 | 7/2007 | Francischelli et al. |
| 7,258,688 B1 | 8/2007 | Shah et al. |
| 7,364,578 B2 | 4/2008 | Francischelli et al. |
| 7,367,972 B2 | 5/2008 | Francischelli et al. |
| 7,381,200 B2 | 6/2008 | Katoh et al. |
| 7,390,894 B2 | 6/2008 | Weinshilboum et al. |
| 7,429,261 B2 | 9/2008 | Kunis et al. |
| 7,533,002 B2 | 5/2009 | Godara |
| 7,582,084 B2 | 9/2009 | Swanson et al. |
| 7,596,469 B2 | 9/2009 | Godara |
| 7,617,005 B2 | 11/2009 | Demarais et al. |
| 7,620,451 B2 | 11/2009 | Demarais et al. |
| 7,647,115 B2 | 1/2010 | Levin et al. |
| 7,651,492 B2 | 1/2010 | Wham |
| 7,653,438 B2 | 1/2010 | Deem et al. |
| 7,717,909 B2 | 5/2010 | Strul et al. |
| 7,717,948 B2 | 5/2010 | Demarais et al. |
| 7,778,703 B2 | 8/2010 | Gross et al. |
| 7,792,589 B2 | 9/2010 | Levy, Jr. et al. |
| 7,799,020 B2 | 9/2010 | Shores et al. |
| 7,824,399 B2 | 11/2010 | Francischelli et al. |
| 7,837,679 B2 | 11/2010 | Biggs et al. |
| 7,842,076 B2 | 11/2010 | Zikorus et al. |
| 7,846,160 B2 | 12/2010 | Payne et al. |
| 7,887,534 B2 | 2/2011 | Hamel et al. |
| 7,901,400 B2 | 3/2011 | Wham et al. |
| 7,922,714 B2 | 4/2011 | Stevens-Wright |
| 7,927,328 B2 | 4/2011 | Orszulak et al. |
| 7,959,626 B2 | 6/2011 | Hong et al. |
| 7,963,962 B2 | 6/2011 | Thompson et al. |
| 7,972,328 B2 | 7/2011 | Wham et al. |
| 7,976,540 B2 | 7/2011 | Daw et al. |
| 8,048,070 B2 | 11/2011 | O'Brien et al. |
| 8,058,771 B2 | 11/2011 | Giordano et al. |
| 8,080,008 B2 | 12/2011 | Wham et al. |
| 8,086,315 B2 | 12/2011 | Schwartz et al. |
| 8,095,212 B2 | 1/2012 | Sato |
| 8,105,323 B2 | 1/2012 | Buysse et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,147,485 B2 | 4/2012 | Wham et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,801 B2 | 4/2012 | Goldberg et al. |
| 8,152,802 B2 | 4/2012 | Podhajsky et al. |
| 8,162,932 B2 | 4/2012 | Podhajsky et al. |
| 8,175,711 B2 | 5/2012 | Demarais et al. |
| 8,241,275 B2 | 8/2012 | Hong et al. |
| 8,273,084 B2 | 9/2012 | Kunis et al. |
| 8,340,763 B2 | 12/2012 | Levin et al. |
| 8,702,619 B2 | 4/2014 | Wang |
| 8,768,470 B2 | 7/2014 | Deem et al. |
| 8,876,813 B2 | 11/2014 | Min et al. |
| 8,909,316 B2 | 12/2014 | Ng |
| 8,977,359 B2 | 3/2015 | Rossing |
| 9,002,446 B2 | 4/2015 | Wenzel et al. |
| 9,014,809 B2 | 4/2015 | Wenzel et al. |
| 9,014,821 B2 | 4/2015 | Wang |
| 2001/0014802 A1 | 8/2001 | Tu |
| 2002/0062123 A1 | 5/2002 | McClurken et al. |
| 2002/0087208 A1 | 7/2002 | Koblish et al. |
| 2002/0091381 A1 | 7/2002 | Edwards |
| 2002/0091385 A1 | 7/2002 | Paton et al. |
| 2002/0107515 A1 | 8/2002 | Edwards et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0004510 A1 | 1/2003 | Wham et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0065322 A1 | 4/2003 | Panescu et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0195507 A1 | 10/2003 | Stewart et al. |
| 2003/0199863 A1 | 10/2003 | Swanson et al. |
| 2003/0216792 A1 | 11/2003 | Levin et al. |
| 2003/0233099 A1 | 12/2003 | Danaek et al. |
| 2004/0010289 A1 | 1/2004 | Biggs et al. |
| 2004/0068304 A1 | 4/2004 | Paton et al. |
| 2004/0122420 A1 | 6/2004 | Amoah |
| 2004/0167509 A1 | 8/2004 | Taimisto |
| 2004/0215186 A1 | 10/2004 | Cornelius et al. |
| 2005/0021020 A1 | 1/2005 | Blaha |
| 2005/0080409 A1 | 4/2005 | Young et al. |
| 2005/0187579 A1 | 8/2005 | Danek et al. |
| 2005/0228460 A1 | 10/2005 | Levin et al. |
| 2005/0283148 A1 | 12/2005 | Janssen et al. |
| 2006/0025765 A1 | 2/2006 | Landman et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0106375 A1 | 5/2006 | Werneth et al. |
| 2006/0142753 A1 | 6/2006 | Francischelli et al. |
| 2006/0161148 A1 | 7/2006 | Behnke |
| 2006/0206150 A1 | 9/2006 | Demarais et al. |
| 2006/0212076 A1 | 9/2006 | Demarais et al. |
| 2006/0271111 A1 | 11/2006 | Demarais et al. |
| 2007/0016274 A1 | 1/2007 | Boveja et al. |
| 2007/0083193 A1 | 4/2007 | Werneth et al. |
| 2007/0083195 A1 | 4/2007 | Werneth et al. |
| 2007/0112342 A1 | 5/2007 | Pearson et al. |
| 2007/0129720 A1 | 6/2007 | Demarais et al. |
| 2007/0167943 A1 | 7/2007 | Janssen et al. |
| 2007/0173805 A1 | 7/2007 | Weinberg et al. |
| 2007/0203481 A1 | 8/2007 | Gregg et al. |
| 2007/0208333 A1 | 9/2007 | Uchida et al. |
| 2007/0265687 A1 | 11/2007 | Deem et al. |
| 2007/0270795 A1 | 11/2007 | Francischelli et al. |
| 2008/0015562 A1 | 1/2008 | Hong et al. |
| 2008/0071257 A1 | 3/2008 | Kotmel et al. |
| 2008/0077126 A1 | 3/2008 | Rashidi |
| 2008/0101356 A1 | 5/2008 | Babbar et al. |
| 2008/0147057 A1 | 6/2008 | Eisele |
| 2008/0188912 A1 | 8/2008 | Stone et al. |
| 2008/0188913 A1 | 8/2008 | Stone et al. |
| 2008/0228181 A1 | 9/2008 | Godara et al. |
| 2008/0262489 A1 | 10/2008 | Steinke |
| 2008/0281312 A1 | 11/2008 | Werneth et al. |
| 2008/0281322 A1 | 11/2008 | Sherman et al. |
| 2008/0300589 A1 | 12/2008 | Paul et al. |
| 2008/0319513 A1 | 12/2008 | Pu et al. |

(56) References Cited

U.S. PATENT DOCUMENTS

| | | |
|---|---|---|
| 2009/0030477 A1 | 1/2009 | Jarrard |
| 2009/0036948 A1 | 2/2009 | Levin et al. |
| 2009/0182323 A1 | 7/2009 | Eder et al. |
| 2009/0182325 A1 | 7/2009 | Werneth et al. |
| 2009/0299365 A1 | 12/2009 | Stewart et al. |
| 2010/0137860 A1 | 6/2010 | Demarais et al. |
| 2010/0137952 A1 | 6/2010 | Demarais et al. |
| 2010/0179533 A1 | 7/2010 | Podhajsky |
| 2010/0179538 A1 | 7/2010 | Podhajsky |
| 2010/0191112 A1 | 7/2010 | Demarais et al. |
| 2010/0211063 A1 | 8/2010 | Wham et al. |
| 2010/0222851 A1 | 9/2010 | Deem et al. |
| 2010/0222854 A1 | 9/2010 | Demarais et al. |
| 2010/0228247 A1 | 9/2010 | Paul et al. |
| 2010/0324548 A1 | 12/2010 | Godara et al. |
| 2011/0077641 A1 | 3/2011 | Dunning |
| 2011/0087214 A1 | 4/2011 | Giordano et al. |
| 2011/0087217 A1 | 4/2011 | Yates et al. |
| 2011/0112400 A1 | 5/2011 | Emery et al. |
| 2011/0130755 A1 | 6/2011 | Bhushan et al. |
| 2011/0190755 A1 | 8/2011 | Mathur et al. |
| 2011/0230876 A1 | 9/2011 | Hong et al. |
| 2011/0270120 A1 | 11/2011 | McFarlin et al. |
| 2011/0270237 A1 | 11/2011 | Werneth et al. |
| 2011/0270247 A1 | 11/2011 | Sherman |
| 2011/0306851 A1 | 12/2011 | Wang |
| 2012/0029504 A1 | 2/2012 | Afonso et al. |
| 2012/0041502 A1 | 2/2012 | Schwartz et al. |
| 2012/0095461 A1 | 4/2012 | Herscher et al. |
| 2012/0101538 A1 | 4/2012 | Ballakur et al. |
| 2012/0123400 A1 | 5/2012 | Francischelli et al. |
| 2012/0130289 A1 | 5/2012 | Demarais et al. |
| 2012/0130345 A1 | 5/2012 | Levin et al. |
| 2012/0136346 A1 | 5/2012 | Condie et al. |
| 2012/0136348 A1 | 5/2012 | Condie et al. |
| 2012/0143097 A1 | 6/2012 | Pike, Jr. |
| 2012/0150169 A1 | 6/2012 | Zielinksi et al. |
| 2012/0172837 A1 | 7/2012 | Demarais et al. |
| 2012/0172870 A1 | 7/2012 | Jenson et al. |
| 2012/0191079 A1 | 7/2012 | Moll et al. |
| 2012/0197243 A1 | 8/2012 | Sherman et al. |
| 2012/0296232 A1 | 11/2012 | Ng |
| 2012/0296329 A1 | 11/2012 | Ng |
| 2012/0310241 A1 | 12/2012 | Orszulak |
| 2013/0006228 A1 | 1/2013 | Johnson et al. |
| 2013/0006235 A1 | 1/2013 | Podhajsky et al. |
| 2013/0072926 A1 | 3/2013 | Hong et al. |
| 2013/0085489 A1 | 4/2013 | Fain et al. |
| 2013/0123778 A1 | 5/2013 | Richardson et al. |
| 2013/0165764 A1 | 6/2013 | Scheuermann et al. |
| 2013/0172878 A1 | 7/2013 | Smith |
| 2013/0218029 A1 | 8/2013 | Cholette et al. |
| 2013/0274614 A1 | 10/2013 | Shimada et al. |
| 2013/0282001 A1 | 10/2013 | Hezi-Yamit et al. |
| 2014/0012133 A1 | 1/2014 | Sverdlik et al. |
| 2014/0012242 A1 | 1/2014 | Lee et al. |
| 2014/0066803 A1 | 3/2014 | Choi |
| 2014/0073903 A1 | 3/2014 | Weber et al. |
| 2014/0074089 A1 | 3/2014 | Nishii |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0228614 A1 | 8/2014 | Stopek |
| 2014/0228829 A1 | 8/2014 | Schmitt et al. |
| 2014/0228858 A1 | 8/2014 | Stopek |
| 2014/0236137 A1 | 8/2014 | Tran et al. |
| 2014/0236138 A1 | 8/2014 | Tran et al. |
| 2014/0246465 A1 | 9/2014 | Peterson et al. |
| 2014/0249524 A1 | 9/2014 | Kocur |
| 2014/0257266 A1 | 9/2014 | Kasprzyk et al. |
| 2014/0266235 A1 | 9/2014 | Mathur |
| 2014/0275924 A1 | 9/2014 | Min et al. |
| 2014/0276124 A1 | 9/2014 | Cholette et al. |
| 2014/0276733 A1 | 9/2014 | VanScoy et al. |
| 2014/0276742 A1 | 9/2014 | Nabutovsky et al. |
| 2014/0276746 A1 | 9/2014 | Nabutovsky et al. |
| 2014/0276755 A1 | 9/2014 | Cao et al. |
| 2014/0276762 A1 | 9/2014 | Parsonage |
| 2014/0276766 A1 | 9/2014 | Brotz et al. |
| 2014/0276767 A1 | 9/2014 | Brotz et al. |
| 2014/0276773 A1 | 9/2014 | Brotz et al. |
| 2014/0316400 A1 | 10/2014 | Blix et al. |
| 2014/0316496 A1 | 10/2014 | Masson et al. |
| 2014/0330266 A1 | 11/2014 | Thompson et al. |
| 2014/0330267 A1 | 11/2014 | Harrington |
| 2014/0336637 A1 | 11/2014 | Agrawal et al. |
| 2015/0005764 A1 | 1/2015 | Hanson et al. |
| 2015/0025524 A1 | 1/2015 | Nabutovsky |
| 2015/0112329 A1 | 4/2015 | Ng |
| 2015/0223877 A1 | 8/2015 | Behar et al. |

FOREIGN PATENT DOCUMENTS

| | | |
|---|---|---|
| EP | 1366724 | 12/2003 |
| EP | 2316371 | 5/2011 |
| EP | 2460486 | 6/2012 |
| EP | 2594193 | 5/2013 |
| EP | 2613704 | 7/2013 |
| EP | 2747691 | 7/2014 |
| EP | 2797535 | 11/2014 |
| JP | 2002065626 | 3/2002 |
| WO | WO-9308757 | 5/1993 |
| WO | WO-9407446 | 4/1994 |
| WO | WO-9410922 | 5/1994 |
| WO | WO-9525472 | 9/1995 |
| WO | WO-9531142 | 11/1995 |
| WO | WO-9600036 | 1/1996 |
| WO | WO-9639086 | 12/1996 |
| WO | WO-9704702 | 2/1997 |
| WO | WO-9736548 | 10/1997 |
| WO | WO-9740882 | 11/1997 |
| WO | WO-9900060 | 1/1999 |
| WO | WO-9960923 | 12/1999 |
| WO | WO-0015130 | 3/2000 |
| WO | WO-0122897 | 4/2001 |
| WO | WO-0170114 | 9/2001 |
| WO | WO-03022167 | 3/2003 |
| WO | WO-03/082080 | 10/2003 |
| WO | WO-2005030072 | 4/2005 |
| WO | WO-2005041748 | 5/2005 |
| WO | WO-2005051215 | 6/2005 |
| WO | WO-2005110528 | 11/2005 |
| WO | WO-2006041881 | 4/2006 |
| WO | WO-2006080982 | 8/2006 |
| WO | WO-2006105121 | 10/2006 |
| WO | WO-2007008954 | 1/2007 |
| WO | WO-2007067941 | 6/2007 |
| WO | WO-2007078997 | 7/2007 |
| WO | WO-2008049084 | 4/2008 |
| WO | WO-2008101356 | 8/2008 |
| WO | WO-2010078175 | 7/2010 |
| WO | WO-2011017168 | 2/2011 |
| WO | WO-2011126580 | 10/2011 |
| WO | WO-2011144911 | 11/2011 |
| WO | WO-2012024631 | 2/2012 |
| WO | WO-2012033974 | 3/2012 |
| WO | WO 2012054762 | 4/2012 |
| WO | WO-2012061153 | 5/2012 |
| WO | WO-2012158864 | 11/2012 |
| WO | WO-2013030738 | 3/2013 |
| WO | WO-2013030743 | 3/2013 |
| WO | WO-2013074813 | 5/2013 |
| WO | WO-2013101485 | 7/2013 |
| WO | WO-2013112844 | 8/2013 |
| WO | WO-2014012282 | 1/2014 |
| WO | WO-2014029355 | 2/2014 |
| WO | WO-2014059165 | 4/2014 |
| WO | WO-2014068577 | 5/2014 |
| WO | WO-2014091328 | 6/2014 |
| WO | WO-2014091401 | 6/2014 |
| WO | WO-2014/124241 | 8/2014 |
| WO | WO-2014/149550 | 9/2014 |
| WO | WO-2014/149552 | 9/2014 |

(56) References Cited

FOREIGN PATENT DOCUMENTS

| WO | WO-2014/149553 | 9/2014 |
|---|---|---|
| WO | WO-2014/149690 | 9/2014 |
| WO | WO-2014150425 | 9/2014 |
| WO | WO-2014150432 | 9/2014 |
| WO | WO-2014150441 | 9/2014 |
| WO | WO-2014150455 | 9/2014 |
| WO | WO-2014/158713 | 10/2014 |
| WO | WO-2014158708 | 10/2014 |
| WO | WO-2014163990 | 10/2014 |
| WO | WO-2014/179110 | 11/2014 |
| WO | WO-2014/179768 | 11/2014 |
| WO | WO-2014/182946 | 11/2014 |

OTHER PUBLICATIONS

Avitall et al., "The creation of linear contiguous lesions in the atria with an expandable loop catheter,"Journal of the American College of Cardiology, 1999; 33; pp. 972-984.

Beale et al., "Minimally Invasive Treatment for Varicose Veins: A Review of Endovenous Laser Treatment and Radiofrequency Ablation". Lower Extremity Wounds 3(4), 2004, 10 pages.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

ClinicalTrials.gov, Renal Denervation in Patients with uncontrolled Hypertension in Chinese (2011), 6pages. www.clinicaltrials.gov/ct2/show/NCT01390831.

Excerpt of Operator's Manual of Boston Scientific's EPT-1000 XP Cardiac Ablation Controller & Accessories, Version of Apr. 2003, (6 pages).

Excerpt of Operator's Manual of Boston Scientific's Maestro 30000 Cardiac Ablation System, Version of Oct. 17, 2005 , (4 pages).

Schneider, Peter A., "Endovascular Skills—Guidewire and Catheter Skills for Endovascular Surgery," Second Edition Revised and Expanded, 10 pages, (2003).

Kandarpa, Krishna et al., "Handbook of Interventional Radiologic Procedures", Third Edition, pp. 194-210 (2002).

ThermoCool Irrigated Catheter and Integrated Ablation System, Biosense Webster (2006), 6 pages.

Mount Sinai School of Medicine clinical trial for Impact of Renal Sympathetic Denervation of Chronic Hypertension, Mar. 2013, 11 pages. http://clinicaltrials.gov/ct2/show/NCT01628198.

Opposition to European Patent No. EP2092957, Granted Jan. 5, 2011, Date of Opposition Oct. 5, 2011, 26 pages.

Opposition to European Patent No. EP1802370, Granted Jan. 5, 2011, Date of Opposition Oct. 5, 2011, 20 pages.

Opposition to European Patent No. EP2037840, Granted Dec. 7, 2011, Date of Opposition Sep. 7, 2012, 25 pages.

Oz, Mehmet, Pressure Relief, Time, Jan. 9, 2012, 2 pages. <www.time.come/time/printout/0,8816,2103278,00.html>.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Pulmonary Vein Stenosis Following Catheter Ablation of Atrial Fibrillation, Curr. Opin. Cardio. 20: 484-490, 2005.

Papademetriou, Vasilios, Renal Sympathetic Denervation for the Treatment of Difficult-to-Control or Resistant Hypertension, Int. Journal of Hypertension, 2011, 8 pages.

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

Wittkampf et al., "Control of radiofrequency lesion size by power regulation," Journal of the American Heart Associate, 1989, 80: pp. 962-968.

Zheng et al., "Comparison of the temperature profile and pathological effect at unipolar, bipolar and phased radiofrequency current configurations," Journal of Interventional Cardiac Electrophysiology, 2001, pp. 401-410.

U.S. Appl. No. 60/852,787, filed Oct. 18, 2006, 112 pages.

Pieper et al., "Design and Implementation of a New Computerized System for Intraoperative Cardiac Mapping." Journal of Applied Physiology, 1991, vol. 71, No. 4, pp. 1529-1539.

Allen, E.V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361; 9, 3 pages.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.

Page, I.H. et al., "The Effect of Renal Denervation on Patients Suffering From Nephritis," Feb. 27, 1935;443-458.

Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009, 4 pages.

Schlaich, M.P. et al., "Renal Denervation as a Therapeutic Approach for Hypertension: Novel Implications for an Old Concept," Hypertension, 2009; 54:1195-1201.

Schlaich, M.P. et al., "Renal Sympathetic-Nerve Ablation for Uncontrolled Hypertension," N Engl J Med 2009; 361(9): 932-934.

Smithwick, R.H. et al., "Splanchnicectomy for Essential Hypertension," Journal Am Med Assn, 1953; 152:1501-1504.

Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.

(56) References Cited

OTHER PUBLICATIONS

Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul lntegr Comp Physiol 1997, vol. 272, 1997 the American Physiological Society, pp. 2034-2039.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news—latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards[TM]" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul lntegr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol,*174: 1592-1594 (2000).
Han, Y.-M, et al., "Renal artery ebolization with diluted hot contrast medium: An experimental study." J Vasc Intery Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.

(56) References Cited

OTHER PUBLICATIONS

Huang et al., "Renal denervation prevents and reverses hyperinsulinemia-induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) Jun. 28, 2011 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
International Search Report and Written Opinion for International App. No. PCT/US2014/061805, mailed Jan. 5, 2015, 11 pages.
Chinushi et al., "Blood Pressure and Autonomic Responses to Electrical Stimulation of the Renal Arterial Nerves Before and After Ablation of the Renal Artery." Hypertension, 2013, 61, pp. 450-456.
Pokushalov et al., "A Randomized Comparison of Pulmonary Vein Isolation With Versus Without Concomitant Renal Artery Denervation in Patients With Refractory Symptomatic Atrial Fibrillation and Resistant Hypertension." Journal of the American College of Cardiology, 2012, 8 pages.

(56) References Cited

OTHER PUBLICATIONS

International Search Report and Written Opinion for International Application No. PC/2011/057740, mailed Jan. 25, 2012, 15 pages.

European Search Report for European Application No. 13159256, Date Mailed: Oct. 17, 2013, 6 pages.

Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.

*Arterial Vasculature*

*Venous Vasculature*

DEVICES, SYSTEMS AND METHODS FOR EVALUATION AND FEEDBACK OF NEUROMODULATION TREATMENT

CROSS-REFERENCE TO RELATED APPLICATION(S)

This application is a continuation of U.S. patent application Ser. No. 13/281,269, filed Oct. 25, 2011, now U.S. Pat. No. 9,066,720, which claims the benefit of the following applications:
(a) U.S. Provisional Application No. 61/406,531, filed Oct. 25, 2010;
(b) U.S. Provisional Application No. 61/528,108, filed Aug. 26, 2011;
(c) U.S. Provisional Application No. 61/528,091, filed Aug. 26, 2011; and
(d) U.S. Provisional Application No. 61/528,684, filed Aug. 29, 2011.

All of the foregoing applications are incorporated herein by reference in their entireties. Further, components and features of embodiments disclosed in the applications incorporated by reference may be combined with various components and features disclosed and claimed in the present application.

TECHNICAL FIELD

The present disclosure relates to neuromodulation treatment and, more particularly, to devices, systems, and methods for providing evaluation and feedback to an operator of a device providing neuromodulation treatment.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine (NE) spillover rates in patients with essential hypertension.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end stage renal disease. In patients with end stage renal disease, NE plasma levels above the median have been demonstrated to be predictive for cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Accordingly, there is a strong public-health need for alternative treatment strategies.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1:
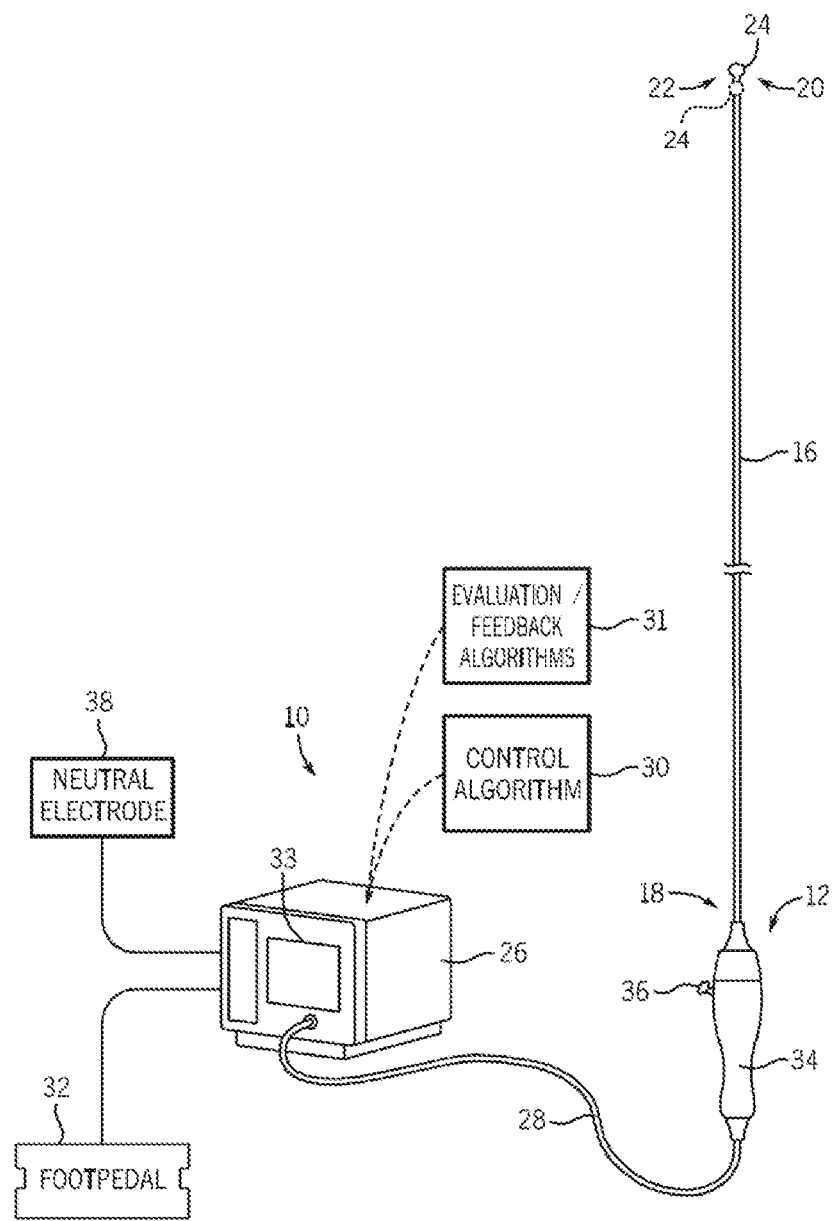
FIG. 1 illustrates a renal neuromodulation system configured in accordance with an embodiment of the present technology.

The present technology is generally directed to devices, systems, and methods for providing useful evaluation and feedback to a clinician or other practitioner performing a procedure, such as electrically- and/or thermally-induced renal neuromodulation (i.e., rendering neural fibers that innervate the kidney inert or inactive or otherwise completely or partially reduced in function). In one embodiment, for example, the feedback relates to a completed treatment and, in particular, to assessment of the likelihood that the treatment was technically successful. In some embodiments, one or more parameters (such as parameters related to temperature, impedance, vessel constriction, heart rate, blood flow, and/or patient motion) monitored over the course of the treatment may be analyzed based on defined criteria. Based on this analysis, an indication may be provided to the operator as to the acceptability or lack of acceptability of the treatment based on the likelihood of technical success by the treatment.

In other embodiments, feedback and/or instructions may be provided to the operator regarding a treatment that failed to complete, such as a procedure that was aborted due to a monitored value associated with temperature or impedance exceeding a predefined and/or calculated threshold or the value being determined to be outside of a predefined and/or calculated range. In such embodiments, one or more parameters (such as parameters related to temperature, impedance, and/or patient motion) monitored over the course of the incomplete treatment may be analyzed based on defined criteria. Based on this analysis, additional instructions or feedback may be provided to the operator, such as whether the treatment site should be imaged to assess whether the treatment device may have inadvertently moved, or whether additional attempts at treatment may be performed, and so forth.

Specific details of several embodiments of the technology are described below with reference to FIGS. 1-14B. Although many of the embodiments are described below with respect to devices, systems, and methods for evaluating neuromodulation treatment, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-14B.

The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

I. Renal Neuromodulation

Renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and in particular conditions associated with central sympathetic over stimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, and sudden death. The reduction of afferent neural signals contributes to the systemic reduction of sympathetic tone/drive, and renal neuromodulation is expected to be useful in treating several conditions associated with systemic sympathetic over activity or hyperactivity. Renal neuromodulation can potentially benefit a variety of organs and bodily structures innervated by sympathetic nerves. For example, a reduction in central sympathetic drive may reduce insulin resistance that afflicts patients with metabolic syndrome and Type II diabetics. Additionally, osteoporosis can be sympathetically activated and might benefit from the downregulation of sympathetic drive that accompanies renal neuromodulation. A more detailed description of pertinent patient anatomy and physiology is provided in Section IV below.

Various techniques can be used to partially or completely incapacitate neural pathways, such as those innervating the kidney. The purposeful application of energy (e.g., electrical energy, thermal energy) to tissue by energy delivery element(s) can induce one or more desired thermal heating effects on localized regions of the renal artery and adjacent regions of the renal plexus RP, which lay intimately within or adjacent to the adventitia of the renal artery. The purposeful application of the thermal heating effects can achieve neuromodulation along all or a portion of the renal plexus RP.

The thermal heating effects can include both thermal ablation and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration.

More specifically, exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity ("RSNA") is expected. A more detailed description of pertinent patient anatomy and physiology is provided in Section IV below.

II. Systems and Methods for Renal Neuromodulation

FIG. 1 illustrates a renal neuromodulation system 10 ("system 10") configured in accordance with an embodiment of the present technology. The system 10 includes an intravascular treatment device 12 operably coupled to an energy source or energy generator 26. In the embodiment shown in FIG. 1, the treatment device 12 (e.g., a catheter) includes an elongated shaft 16 having a proximal portion 18, a handle assembly 34 at a proximal region of the proximal portion 18, and a distal portion 20 extending distally relative to the proximal portion 18. The treatment device 12 further includes a therapeutic assembly or treatment section 22 including an energy delivery element 24 (e.g., an electrode) at or near the distal portion 20 of the shaft 16. In the illustrated embodiment, a second energy delivery element 24 is illustrated in broken lines to indicate that the systems and methods disclosed herein can be used with treatment devices having one or more energy delivery elements 24. Further, it will be appreciated that although only two energy delivery elements 24 are shown, the treatment device 12 may include additional energy delivery elements 24.

The energy generator 26 (e.g., a RF energy generator) is configured to generate a selected form and magnitude of energy for delivery to the target treatment site via the energy delivery element 24. The energy generator 26 can be electrically coupled to the treatment device 12 via a cable 28. At least one supply wire (not shown) passes along the elongated shaft 16 or through a lumen in the elongated shaft 16 to the energy delivery element 24 and transmits the treatment energy to the energy delivery element 24. A control mechanism, such as foot pedal 32, may be connected (e.g., pneumatically connected or electrically connected) to the energy generator 26 to allow the operator to initiate, terminate and, optionally, adjust various operational characteristics of the energy generator, including, but not limited to, power delivery. The energy generator 26 can be configured to deliver the treatment energy via an automated control algorithm 30 and/or under the control of a clinician. In addition, one or more evaluation/feedback algorithms 31 may be executed on a processor of the system 10. Such evaluation/feedback algorithms 31, when executed in conjunction with a treatment operation, may provide feedback to a user of the system 10, such as via a display 33 associated with the system 10. The feedback or evaluation may allow an operator of the system 10 to determine the success of a given treatment and/or to evaluate possible failure conditions. This feedback, therefore, may be useful in helping the operator learn how to increase the likelihood of success when performing a treatment. Further details regarding suitable control algorithms 30 and evaluation/feedback algorithms 31 are described below with reference to FIGS. 3-10B.

Figure 2:
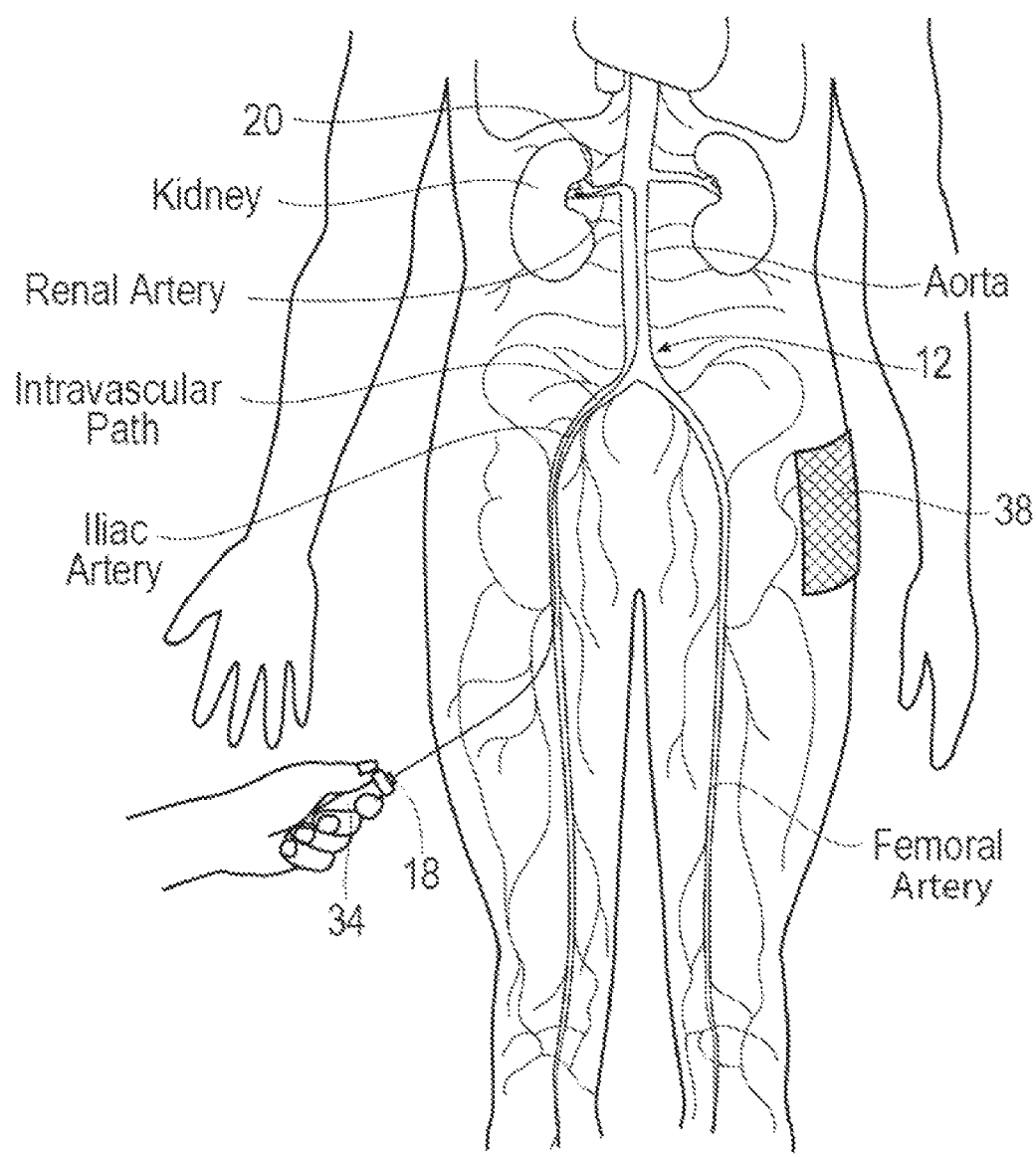
FIG. 2 illustrates modulating renal nerves with a catheter apparatus in accordance with an embodiment of the technology.

In some embodiments, the system 10 may be configured to provide delivery of a monopolar electric field via the energy delivery element 24. In such embodiments, a neutral or dispersive electrode 38 may be electrically connected to the energy generator 26 and attached to the exterior of the patient (as shown in FIG. 2). Additionally, one or more sensors (not shown), such as one or more temperature (e.g., thermocouple, thermistor, etc.), impedance, pressure, optical, flow, chemical or other sensors, may be located proximate to or within the energy delivery element 24 and connected to one or more of the supply wires (not shown). For example, a total of two supply wires may be included, in which both wires could transmit the signal from the sensor and one wire could serve dual purpose and also convey the energy to the energy delivery element 24. Alternatively, both wires could transmit energy to the energy delivery element 24.

In embodiments including multiple energy delivery element 24, the energy delivery elements 24 may deliver power independently (i.e., may be used in a monopolar fashion), either simultaneously, selectively, or sequentially, and/or may deliver power between any desired combination of the elements (i.e., may be used in a bipolar fashion). Furthermore, the clinician optionally may be permitted to choose which energy delivery element(s) 24 are used for power delivery in order to form highly customized lesion(s) within the renal artery, as desired.

The computing devices on which the system 10 is implemented may include a central processing unit, memory, input devices (e.g., keyboard and pointing devices), output devices (e.g., display devices), and storage devices (e.g., disk drives). The output devices may be configured to communicate with the treatment device 12 (e.g., via the cable 28) to control power to the energy delivery element 24 and/or to obtain signals from the energy delivery element 24 or any associated sensors. Display devices may be configured to provide indications of power levels or sensor data, such as audio, visual or other indications, or may be configured to communicate the information to another device.

The memory and storage devices are computer-readable media that may be encoded with computer-executable instructions that implement the object permission enforcement system, which means a computer-readable medium that contains the instructions. In addition, the instructions, data structures, and message structures may be stored or transmitted via a data transmission medium, such as a signal on a communications link and may be encrypted. Various communications links may be used, such as the Internet, a local area network, a wide area network, a point-to-point dial-up connection, a cell phone network, and so on.

Embodiments of the system 10 may be implemented in and used with various operating environments that include personal computers, server computers, handheld or laptop devices, multiprocessor systems, microprocessor-based systems, programmable consumer electronics, digital cameras, network PCs, minicomputers, mainframe computers, computing environments that include any of the above systems or devices, and so on.

The system 10 may be described in the general context of computer-executable instructions, such as program modules, executed by one or more computers or other devices. Generally, program modules include routines, programs, objects, components, data structures, and so on that perform particular tasks or implement particular abstract data types. Typically, the functionality of the program modules may be combined or distributed as desired in various embodiments.

FIG. 2 (and with reference to FIG. 12) illustrates modulating renal nerves with an embodiment of the system 10. The treatment device 12 provides access to the renal plexus RP through an intravascular path, such as from a percutaneous access site in the femoral (illustrated), brachial, radial, or axillary artery to a targeted treatment site within a respective renal artery RA. As illustrated, a section of the proximal portion 18 of the shaft 16 is exposed externally of the patient.

By manipulating the proximal portion 18 of the shaft 16 from outside the intravascular path (e.g., via the handle assembly 34), the clinician may advance the shaft 16 through the sometimes tortuous intravascular path and remotely manipulate or actuate the shaft distal portion 20. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12 itself. Once proximity between, alignment with, and contact between the energy delivery element 24 and tissue are established within the respective renal artery, the purposeful application of energy from the energy generator 26 to tissue by the energy delivery element 24 induces one or more desired neuromodulating effects on localized regions of the renal artery and adjacent regions of the renal plexus RP, which lay intimately within, adjacent to, or in close proximity to the adventitia of the renal artery. The purposeful application of the energy may achieve neuromodulation along all or a portion of the renal plexus RP.

The neuromodulating effects are generally a function of, at least in part, power, time, contact between the energy delivery element(s) 24 and the vessel wall, and blood flow through the vessel. The neuromodulating effects may include denervation, thermal ablation, and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

III. Evaluation of Renal Neuromodulation Treatment

A. Overview

In one implementation, a treatment administered using the system 10 constitutes delivering energy through one or more energy delivery elements (e.g., electrodes) to the inner wall of a renal artery for a predetermined amount of time (e.g., 120 sec). Multiple treatments (e.g., 4-6) may be administered in both the left and right renal arteries to achieve the desired coverage. A technical objective of a treatment may be, for example, to heat tissue to a depth of at least about 3 mm to a temperature that would lesion a nerve (e.g., about 65° C.). A clinical objective of the procedure typically is to neuromodulate (e.g., lesion) a sufficient number of renal nerves (either efferent or afferent nerves of the sympathetic renal plexus) to cause a reduction in sympathetic tone. If the technical objective of a treatment is met (e.g., tissue is heated to about 65° C. to a depth of about 3 mm) the probability of forming a lesion of renal nerve tissue is high. The greater the number of technically successful treatments, the greater the probability of modulating a sufficient proportion of renal nerves, and thus the greater the probability of clinical success.

Throughout the treatment there may be a number of states that are indicative of a possibility that the treatment may not be successful. In certain embodiments, based on indications of these states, the operation of the system 10 may be stopped or modified. For example, certain indications may result in cessation of energy delivery and an appropriate message may be displayed, such as on display 33. Factors that may result in a display message and/or cessation or modification of a treatment protocol include, but are not limited to, indications of an impedance, blood flow, and/or temperature measurement or change that is outside of accepted or expected thresholds and/or ranges that may be predetermined or calculated. A message can indicate information such as a type of patient condition (e.g., an abnormal patient condition), the type and/or value of the parameter that falls outside an accepted or expected threshold, an indication of suggested action for a clinician, or an indication that energy delivery has been stopped. However, if no unexpected or aberrant measurements are observed, energy may continue to be delivered at the target site in accordance with a programmed profile for a specified duration resulting in a complete treatment. Following a completed treatment, energy delivery is stopped and a message indicating completion of the treatment may be displayed.

However, a treatment can be completed without initiating an indication of an abnormal patient condition and yet an event or combination of events could occur that alters (e.g., decreases) the probability of a technically successful treatment. For example, an electrode that is delivering energy could move or be inadvertently placed with insufficient contact between the electrode and the wall of a renal artery, thereby resulting in insufficient lesion depth or temperature. Therefore, even when a treatment is completed without an indication of abnormal patient condition, it may be difficult to evaluate the technical success of the treatment. Likewise, to the extent that indications of abnormal patient conditions may be reported by the system 10, it may be difficult to understand the causes of the abnormal patient conditions (such as temperature and/or impedance values that fall outside of expected ranges).

As noted above, one or more evaluation/feedback algorithms 31 may be provided that are executed on a processor-based component of the system 10, such as one or more components provided with the generator 26. In such implementations, the one or more evaluation/feedback algorithms 31 may be able to provide a user with meaningful feedback that can be used in evaluating a given treatment and/or that can be used in learning the significance of certain types of abnormal patient conditions and how to reduce the occurrence of such conditions. For example, if a particular parameter (e.g., an impedance or temperature value) causes or indicates that treatment did not proceed as expected and (in some instances), may have resulted in a technically unsuccessful treatment, the system 10 can provide feedback (e.g., via the display 33) to alert the clinician. The alert to the clinician can range from a simple notification of unsuccessful treatment to a recommendation that a particular parameter of the treatment (e.g., the impedance value(s) during treatment, placement of the energy delivery elements 24 within the patient, etc.) be modified in a subsequent treatment. The system 10 can accordingly learn from completed treatment cycles and modify subsequent treatment parameters based on such learning to improve efficacy. Non-exhaustive examples of measurements the one or more evaluation/feedback algorithms 31 may consider include measurements related to change(s) in temperature over a specified time, a maximum temperature, a maximum average temperature, a minimum temperature, a temperature at a predetermined or calculated time relative to a predetermined or calculated temperature, an average temperature over a specified time, a maximum blood flow, a minimum blood flow, a blood flow at a predetermined or calculated time relative to a predetermined or calculated blood flow, an average blood flow over time, a maximum impedance, a minimum impedance, an impedance at a predetermined or calculated time relative to a predetermined or calculated impedance, a change in impedance over a specified time, or a change in impedance relative to a change in temperature over a specified time. Measurements may be taken at one or more predetermined times, ranges of times, calculated times, and/or times when or relative to when a measured event occurs. It will be appreciated that the foregoing list merely provides a number of examples of different measurements, and other suitable measurements may be used.

B. Control of Applied Energy

Figure 3:
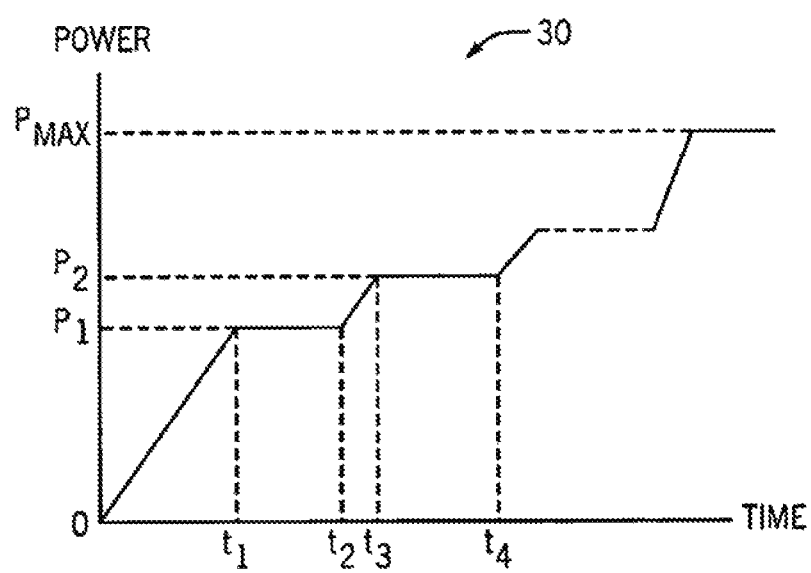
FIG. 3 is a graph depicting an energy delivery algorithm that may be used in conjunction with the system of FIG. 1 in accordance with an embodiment of the technology.

With the treatments disclosed herein for delivering therapy to target tissue, it may be beneficial for energy to be delivered to the target neural structures in a controlled manner. The controlled delivery of energy will allow the zone of thermal treatment to extend into the renal fascia while reducing undesirable energy delivery or thermal effects to the vessel wall. A controlled delivery of energy may also result in a more consistent, predictable and efficient overall treatment. Accordingly, the generator 26 desirably includes a processor including a memory component with instructions for executing an algorithm 30 (see FIG. 1) for controlling the delivery of power and energy to the energy delivery device. The algorithm 30, a representative embodiment of which is depicted in FIG. 3, may be implemented as a conventional computer program for execution by a processor coupled to the generator 26. A clinician using step-by-step instructions may also implement the algorithm 30 manually.

The operating parameters monitored in accordance with the algorithm may include, for example, temperature, time, impedance, power, blood flow, flow velocity, volumetric flow rate, blood pressure, heart rate, etc. Discrete values in temperature may be used to trigger changes in power or energy delivery. For example, high values in temperature (e.g., 85° C.) could indicate tissue desiccation in which case the algorithm may decrease or stop the power and energy delivery to prevent undesirable thermal effects to target or non-target tissue. Time additionally or alternatively may be used to prevent undesirable thermal alteration to non-target tissue. For each treatment, a set time (e.g., 2 minutes) is checked to prevent indefinite delivery of power.

Impedance may be used to measure tissue changes. Impedance indicates the electrical property of the treatment site. In thermal inductive embodiments, when an electric field is applied to the treatment site, the impedance will decrease as the tissue cells become less resistive to current flow. If too much energy is applied, tissue desiccation or coagulation may occur near the electrode, which would increase the impedance as the cells lose water retention and/or the electrode surface area decreases (e.g., via the accumulation of coagulum). Thus, an increase in tissue impedance may be indicative or predictive of undesirable thermal alteration to target or non-target tissue. In other embodiments, the impedance value may be used to assess contact of the energy delivery element(s) 24 with the tissue. For multiple electrode configurations (e.g., when the energy delivery element(s) 24 includes two or more electrodes,) a relatively small difference between the impedance values of the individual electrodes may be indicative of good contact with the tissue. For a single electrode configuration, a stable value may be indicative of good contact. Accordingly, impedance information from the one or more electrodes may be provided to a downstream monitor, which in turn may provide an indication to a clinician related to the quality of the energy delivery element(s) 24 contact with the tissue.

Additionally or alternatively, power is an effective parameter to monitor in controlling the delivery of therapy. Power is a function of voltage and current. The algorithm 30 may tailor the voltage and/or current to achieve a desired power.

Derivatives of the aforementioned parameters (e.g., rates of change) also may be used to trigger changes in power or energy delivery. For example, the rate of change in temperature could be monitored such that power output is reduced in the event that a sudden rise in temperature is detected. Likewise, the rate of change of impedance could be monitored such that power output is reduced in the event that a sudden rise in impedance is detected.

As seen in FIG. 3, when a clinician initiates treatment (e.g., via the foot pedal 32 illustrated in FIG. 1), the control algorithm 30 includes instructions to the generator 26 to gradually adjust its power output to a first power level $P_1$ (e.g., 5 watts) over a first time period $t_1$ (e.g., 15 seconds). The power increase during the first time period is generally linear. As a result, the generator 26 increases its power output at a generally constant rate of $P_1/t_1$. Alternatively, the power increase may be non-linear (e.g., exponential or parabolic) with a variable rate of increase. Once $P_1$ and $t_1$ are achieved, the algorithm may hold at $P_1$ until a new time $t_2$ for a predetermined period of time $t_2-t_1$ (e.g., 3 seconds). At $t_2$ power is increased by a predetermined increment (e.g., 1 watt) to $P_2$ over a predetermined period of time, $t_3-t_2$ (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment $P_{MAX}$ is 10 watts. Optionally, the power may be maintained at the maximum power $P_{MAX}$ for a desired period of time or up to the desired total treatment time (e.g., up to about 120 seconds).

In FIG. 3, the algorithm 30 illustratively includes a power-control algorithm. However, it should be understood that the algorithm 30 alternatively may include a temperature-control algorithm. For example, power may be gradually increased until a desired temperature (or temperatures) is obtained for a desired duration (or durations). In another embodiment, a combination power-control and temperature-control algorithm may be provided.

As discussed, the algorithm 30 includes monitoring certain operating parameters (e.g., temperature, time, impedance, power, flow velocity, volumetric flow rate, blood pressure, heart rate, etc.). The operating parameters may be monitored continuously or periodically. The algorithm 30 checks the monitored parameters against predetermined parameter profiles to determine whether the parameters individually or in combination fall within the ranges set by the predetermined parameter profiles. If the monitored parameters fall within the ranges set by the predetermined parameter profiles, then treatment may continue at the commanded power output. If monitored parameters fall outside the ranges set by the predetermined parameter profiles, the algorithm 30 adjusts the commanded power output accordingly. For example, if a target temperature (e.g., 65° C.) is achieved, then power delivery is kept constant until the total treatment time (e.g., 120 seconds) has expired. If a first temperature threshold (e.g., 70° C.) is achieved or exceeded, then power is reduced in predetermined increments (e.g., 0.5 watts, 1.0 watts, etc.) until a target temperature is achieved. If a second power threshold (e.g., 85° C.) is achieved or exceeded, thereby indicating an undesirable condition, then power delivery may be terminated. The system may be equipped with various audible and visual alarms to alert the operator of certain conditions.

The following is a non-exhaustive list of events under which algorithm 30 may adjust and/or terminate/discontinue the commanded power output:

(1) The measured temperature exceeds a maximum temperature threshold (e.g., from about 70 to about 85° C.).

(2) The average temperature derived from the measured temperature exceeds an average temperature threshold (e.g., about 65° C.).

(3) The rate of change of the measured temperature exceeds a rate of change threshold.

(4) The temperature rise over a period of time is below a minimum temperature change threshold while the generator 26 has non-zero output. Poor contact between the energy delivery element(s) 24 and the arterial wall may cause such a condition.

(5) A measured impedance exceeds or falls outside an impedance threshold (e.g., <20 Ohms or >500 Ohms).

(6) A measured impedance exceeds a relative threshold (e.g., impedance decreases from a starting or baseline value and then rises above this baseline value)

(7) A measured power exceeds a power threshold (e.g., >8 Watts or >10 Watts).

(8) A measured duration of power delivery exceeds a time threshold (e.g., >120 seconds).

Advantageously, the magnitude of maximum power delivered during renal neuromodulation treatment in accordance with the present technology may be relatively low (e.g., less than about 15 Watts, less than about 10 Watts, less than about 8 Watts, etc.) as compared, for example, to the power levels utilized in electrophysiology treatments to achieve cardiac tissue ablation (e.g., power levels greater than about 15 Watts, greater than about 30 Watts, etc.). Since relatively low power levels may be utilized to achieve such renal neuromodulation, the flow rate and/or total volume of intravascular infusate injection needed to maintain the energy delivery element and/or non-target tissue at or below a desired temperature during power delivery (e.g., at or below about 50° C., for example, or at or below about 45° C.) also may be relatively lower than would be required at the higher power levels used, for example, in electrophysiology treatments (e.g., power levels above about 15 Watts). In embodiments in which active cooling is used, the relative reduction in flow rate and/or total volume of intravascular infusate infusion advantageously may facilitate the use of intravascular infusate in higher risk patient groups that would be contraindicated were higher power levels and, thus, correspondingly higher infusate rates/volumes utilized (e.g., patients with heart disease, heart failure, renal insufficiency and/or diabetes mellitus).

C. Technical Evaluation of a Treatment

Figure 4:
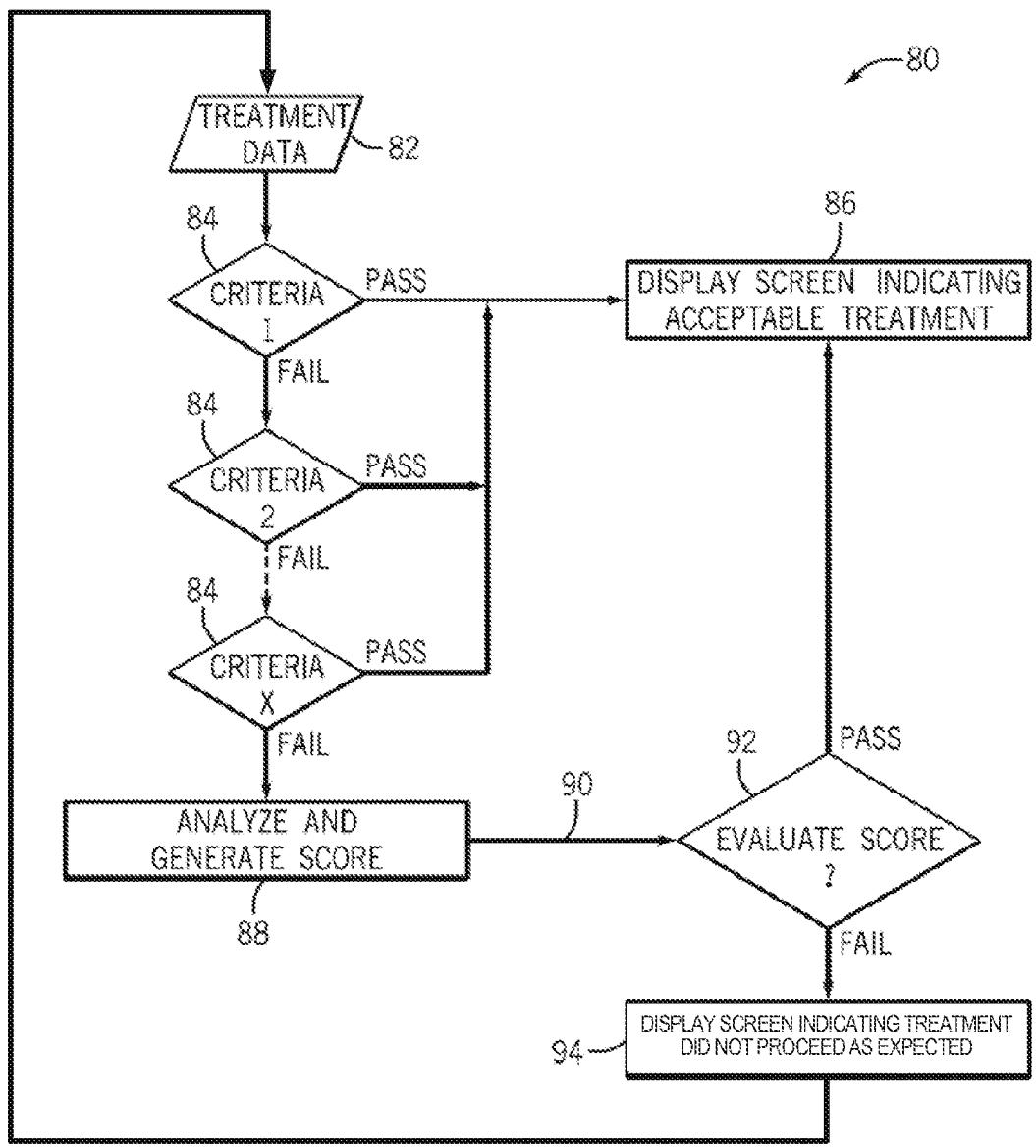
FIGS. 4 and 5 are block diagrams illustrating algorithms for evaluating a treatment in accordance with embodiments of the present technology.

FIG. 4 is a block diagram of a treatment algorithm 80 configured in accordance with an embodiment of the present technology. The algorithm 80 is configured to evaluate events in a treatment, determine the probability of technical success of the treatment and display a message accordingly to provide feedback to an operator of the system 10 (or another suitable treatment system). If the treatment is determined to have a predetermined probability of sub optimal technical success, a message indicating that the treatment did not proceed as expected may be displayed. Alternative implementations can categorize a treatment into several ranges of probabilities of success, such as probability of success on a scale of 1 to 5. Similarly, in certain implementations, the algorithm 80 can evaluate if a treatment belongs in a high probability of success category, a very low probability of success category, or somewhere in between.

Variables that characterize a treatment and that may be used by the algorithm 80 in evaluating a treatment include, but are not limited to: time (i.e., treatment duration), power, change in temperature, maximum temperature, mean temperature, blood flow, standard deviation of temperature or impedance, change in impedance, or combinations of these or other variables. For example, some or all of the variables may be provided to the algorithm 80 as treatment data 82. In this generalized depiction of an algorithm 80, the treatment data 80 may be assessed based on a cascade or series of different categories or degrees of criteria 84. Favorable assessment of the treatment data 82 in view of one of the criteria 84 may result in the display (block 86) of a message indicating the treatment was acceptable or successful. Failure of the treatment data 82 to be found acceptable in view of a criterion 84 may result in the treatment data dropping to the next evaluation criterion 84.

In the depicted embodiment, failure of the treatment data to be found acceptable in view of all of the criteria 84 may result in an additional evaluation being performed, such as the depicted analysis and scoring step 88. The output of the analysis and scoring step (e.g., a score 90) may be evaluated (block 92). Based on this evaluation 92, the treatment may be deemed acceptable, and the corresponding screen displayed (block 86), or not acceptable, and a screen 94 displayed indicating that treatment did not proceed as expected. In still further embodiments, the algorithm 80 can include an automatic action (e.g., automatic reduction of the power level supplied to the energy source) in response to an indication that treatment did not proceed as expected.

Figure 5:
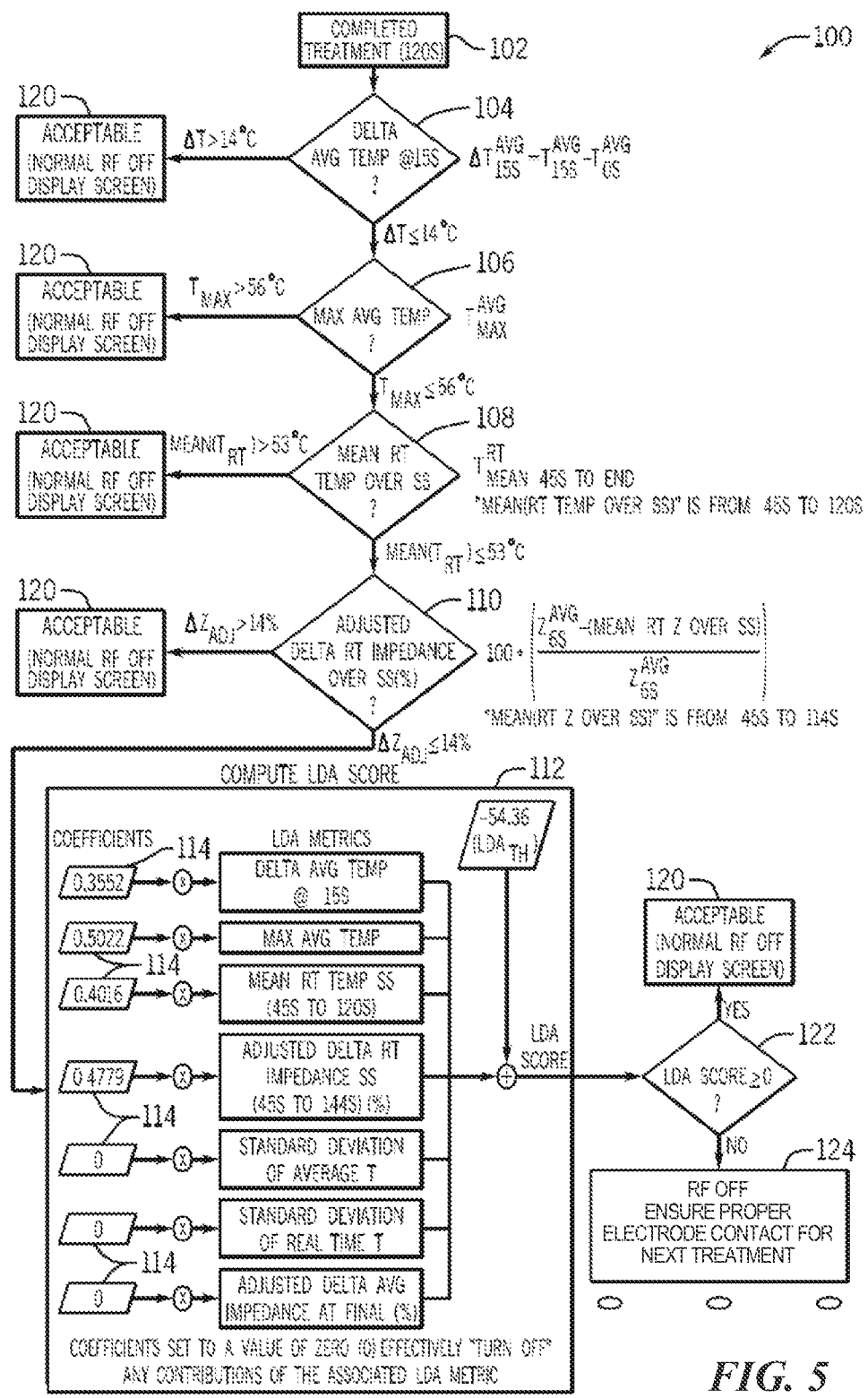

While FIG. 4 depicts a generalized and simplified implementation of a treatment evaluation algorithm, FIG. 5 depicts a more detailed example of one embodiment of a treatment evaluation algorithm 100. The treatment evaluation algorithm 100 may be computed following the completion of a treatment (block 102), which may be 120 seconds long (as depicted) or some other suitable duration, and using data and/or measurements derived over the course of the treatment.

In the depicted embodiment, it is considered likely that the greatest probability of less than ideal treatment occurs when an electrode is not in consistent contact with the vessel wall. Accordingly, decision blocks 104, 106, 108, and 110 in the flowchart are associated with different criteria and screen out those treatments that appear to have one or more criteria outside a pre-determined range (i.e., do not have a high probability of success) based on observed or measured data 102 over the course of the completed treatment. In the depicted embodiment, those treatments that are not screened out at decision blocks 104, 106, 108, and 110 enter a linear discriminant analysis (LDA) 112 to further evaluate the treatment. In other embodiments, other suitable analyses may be performed instead of the depicted LDA. Values assigned to each step (i.e., evaluation by a respective criterion) and coefficients 114 used in the LDA can be derived from data collected from several treatments and/or from experience gained from animal studies.

In the depicted embodiment, the first decision block 104 evaluates the initial temperature response to energy delivery by checking if the change in average temperature in the first 15 seconds is greater than 14° C. In one implementation, average temperature refers to the average over a short amount of time (e.g., 3 seconds), which essentially filters large fluctuations at high frequency caused by pulsatile blood flow. As will be appreciated, a temperature rise in the treatment electrode is a result of heat conducting from tissue to the electrode. If an electrode is not in sufficient contact with a vessel wall, energy is delivered into the blood flowing around it and the temperature of the electrode is not increased as much. With this in mind, if the change in average temperature in the first 15 seconds is greater than, e.g., 14° C., this initial temperature response may indicate sufficient electrode contact, contact force, and/or blood flow rate, at least in the beginning of the treatment and, if no indication that treatment did not proceed as expected is encountered for the remainder of the treatment, there is not a high probability that the treatment was less than optimal or technically unsuccessful. Thus, a positive answer at decision block 104 results in a "Treatment Complete" message 120 being displayed. However, if the change in average temperature in the first 15 seconds is less than or equal to, e.g., 14° C., this initial temperature response may indicate that the electrode may not have had sufficient contact with the vessel wall. Thus, a negative answer at decision block 104 results in proceeding to criteria 106 for further evaluation.

At decision block 106 the hottest temperature is evaluated by checking if the maximum average temperature is greater than, e.g., 56° C. A temperature rise above a threshold level (e.g., 56° C.), regardless of duration, may be enough to allow technical success. Thus, a temperature above threshold may be sufficient to indicate successful lesion formation despite the fact that at decision block 104 the initial rise in temperature did not indicate sufficient contact. For example, the electrode may not have had sufficient contact initially but then contact could have been made at least for enough time to cause the vessel wall to heat up such that the temperature sensor in the electrode reads above 56° C. A positive result at decision block 106 results in a "Treatment Complete" message 120 being displayed. However, a negative result at decision block 106 indicates that the maximum average temperature did not rise enough. The algorithm 100, therefore, proceeds to decision block 108 for further evaluation.

At decision block 108 the mean temperature is evaluated during a period when power is sustained at its maximum amount (i.e., the ramping up period is eliminated from the mean calculation). In one embodiment, this evaluation consists of determining whether the mean real time temperature is above 53° C. during the period from 45 seconds to 120 seconds. In this manner, this criterion checks to determine if temperature was above a threshold for a certain duration. If decision block 108 yields a positive determination then, despite the fact that the initial temperature response and the maximum average temperature were insufficient to indicate technical success (i.e., decision blocks 104 and 106 were failed), the mean temperature during the last 75 seconds indicates sufficient contact for sufficient time. For example, it is possible that a sufficient lesion was made and yet the maximum average temperature measured in the electrode was not greater than 56° C. because there is high blood flow pulling heat from the electrode. Therefore, a positive result at decision block 108 results in a "Treatment Complete" message 120 being displayed. However, a negative result at decision block 108 indicates that the mean real time temperature in the sustained power stage was not sufficient and the algorithm 100 proceeds to decision block 110 for further evaluation of the treatment.

At decision block 110 the change in impedance is evaluated by checking if the percentage of impedance change during a predetermined period of time (e.g., 45 seconds to 114 seconds), is greater than a predetermined value (e.g., 14%) of the initial impedance. The initial impedance is determined as the impedance shortly after the beginning of treatment (e.g., at 6 seconds) to eliminate possible misreadings in impedance measurement prior to this period (e.g., due to contrast injection). As will be appreciated, the impedance of tissue to radiofrequency (RF) electrical current decreases as the tissue temperature increases until the tissue is heated enough to cause it to desiccate at which point its impedance starts to rise. Therefore, a decrease in tissue impedance can indicate a rise in tissue temperature. The percentage change in real time impedance over the sustained power stage may be calculated as follows:

$$\% \, \Delta Z \text{ over } SS = 100 * \left( \frac{Z_{6s}^{avg} - (\text{mean } RT \, Z \text{ over } SS)}{Z_{6s}^{avg}} \right) \quad (1)$$

If decision block 110 yields a positive determination then, despite the fact that the previous three decision blocks failed to show that there was a sufficient rise in temperature (i.e., decision blocks 104, 106, and 108 were failed), the change in impedance could indicate that tissue was heated sufficiently but the temperature sensor in the electrode did not rise enough. For example, very high blood flow could cause the electrode temperature to remain relatively low even if the tissue was heated. Therefore, a positive result at decision block 110 results in a "Treatment Complete" message 120 being displayed. However, a negative result at decision block 110 results in the algorithm 100 proceeding to perform a LDA 112.

At LDA 112, a combination of events is evaluated along with a rating of importance for each event. In the depicted embodiment, for example, the criteria evaluated at decision blocks 104, 106, 108, 110 are included in the LDA 112. In addition, in this implementation, three additional criteria may be included: (1) standard deviation of average temperature (which can provide an indication of the degree of sliding motion caused by respiration); (2) standard deviation of real time temperature (which can provide an indication of variable blood flow and/or contact force and/or intermittent contact); and (3) adjusted change in average impedance at the end of the treatment (which can further characterize change in impedance and provide an indication of change in temperature of tissue). If this analysis determines the combination of variables to have a significant impact on reducing technical success (e.g., a LDA score<0 at decision block 122) then an "Unexpected Treatment" message 124 is displayed. Otherwise, a "Treatment Complete" message 120 is displayed.

It will be appreciated that the various parameters described above are merely representative examples associated with one embodiment of the algorithm 100, and one or more of these parameters may vary in other embodiments. Further, the specific values described above with respect to particular portions of the treatment may be modified/changed in other embodiments based on, for example, different device configurations, electrode configurations, treatment protocols, etc.

As described above, the algorithm 100 is configured to evaluate a treatment and display a message indicating that treatment is complete or, alternatively, that treatment did not proceed as expected. Based on the message describing the evaluation of the treatment, the clinician (or the system using automated techniques) can then decide whether further treatments may be necessary and/or if one or more parameters should be modified in subsequent treatments. In the above-described examples, for example, the algorithm 100 may evaluate a number of situations generally related to poor contact between the electrode and vessel wall to help determine if the treatment was less than optimal. For example, poor contact may occur when an electrode slides back and forth as the patient breaths and the artery moves, when an electrode becomes displaced when a patient moves, when the catheter is moved inadvertently, when a catheter is not deflected to the degree needed to apply sufficient contact or contact force between the electrode and vessel wall, and/or when an electrode is placed in a precarious position. Further, as described above, if a particular parameter or set of parameters may have contributed to or resulted in a less than optimal treatment, the system 10 (FIG. 1) can provide feedback to alert the clinician to modify one or more treatment parameters during a subsequent treatment. Such evaluation and feedback of a treatment is expected to help clinicians learn to improve their placement technique to get better contact and reduce the frequency of technically unsuccessful treatments.

D. Feedback Related to High Temperature Conditions

While the preceding describes generalized evaluation of the technical success of a treatment, another form of feedback that may be useful to an operator of the system 10 (FIG. 1) is feedback related to specific types of patient or treatment conditions. For example, the system 10 may generate a message related to high temperature conditions. In particular, during a treatment while energy is being delivered, tissue temperature may increase above a specified level. A temperature sensor (e.g., thermocouple, thermistor, etc.) positioned in or near the electrode provides an indication of temperature in the electrode and, to some extent, an indication of tissue temperature. The electrode does not heat directly as energy is delivered to tissue. Instead, tissue is heated and the heat conducts to the electrode and the temperature sensor in the electrode. In one implementation, the system 10 may cease energy delivery if the real time temperature rises above a predefined maximum temperature (e.g., 85° C.). In such an event, the system may generate a message indicating the high temperature condition. However, depending on the circumstances, different actions by the clinician may be appropriate.

If tissue becomes too hot, established temperature thresholds can be exceeded. The implications of high tissue temperature are that an acute constriction of the artery or a protrusion of the artery wall could occur. This can happen right away or within a short time (e.g., about 50 seconds to about 100 seconds) after the occurrence of the high temperature is noted and a message is generated. In such an occurrence, the clinician may be instructed to image the treatment site to watch for a constriction or protrusion before starting another treatment.

Figure 6:
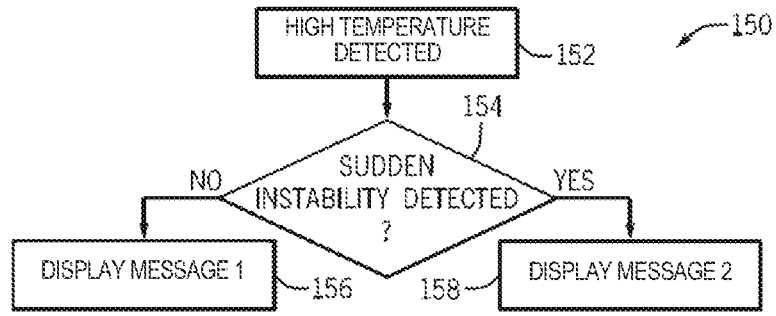
FIG. 6 is a block diagram illustrating an algorithm for providing operator feedback upon occurrence of a high temperature condition in accordance with an embodiment of the present technology.

FIG. 6, for example, is a block diagram illustrating an algorithm 150 for providing operator feedback when a high temperature condition is detected in accordance with an embodiment of the present technology. In one implementation the algorithm 150 is executed in response to a high temperature condition (block 152) and evaluates (decision block 154) data from the treatment to determine if the high temperature condition involved a situation that included sudden instability or if it did not. Sudden instability can be caused, for example, by sudden movement of the patient or catheter, thereby causing the electrode to be pushed harder (i.e., contact force is increased) into the vessel wall, which could also be accompanied by movement to another location. In the event that sudden instability is not detected at decision block 154, a first message may be displayed (block 156), such as an indication that a high temperature has been detected and an instruction to image the treatment site to determine if the site has been damaged. In the event that sudden instability is detected at decision block 154, an alternative message may be displayed (block 158) that, in addition to indicating the occurrence of the high temperature and instructing the clinician to image the treatment site, may also indicate the possibility that the electrode may have moved from its original site. Such feedback may prompt the clinician to compare previous images and avoid treating again on either of the original site or the site to which the electrode has moved.

E. Feedback Related to High Impedance

As with high temperature, in certain circumstances the system 10 (FIG. 1) may generate a message related to the occurrence of high impedance. As will be appreciated, impedance to RF current passing from a treatment electrode through the body to a dispersive return electrode can provide an indication of characteristics of the tissue that is in contact with the treatment electrode. For example, an electrode positioned in the blood stream in a renal artery may measure a lower impedance than an electrode contacting the vessel wall. Furthermore, as tissue temperature rises its impedance decreases. However, if the tissue gets too hot it may desiccate and its impedance may increase. During a treatment as tissue is gradually heated it is expected that impedance will decrease. A significant rise in impedance can be a result of an undesired situation such as tissue desiccation or electrode movement. In certain implementations, the system 10 may be configured to cease energy delivery if the real time impedance rise is higher than a predefined maximum change in impedance from the starting impedance.

Figure 7:
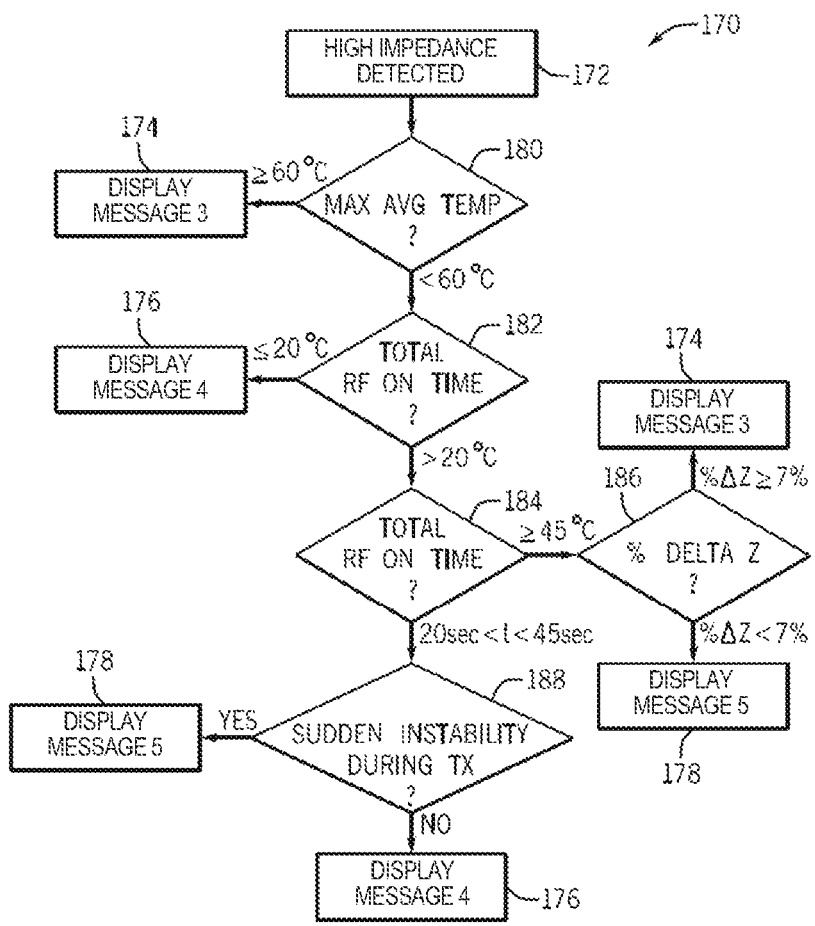
FIG. 7 is a block diagram illustrating an algorithm for providing operator feedback upon occurrence of a high impedance condition in accordance with an embodiment of the present technology.

FIG. 7, for example, is a block diagram illustrating an algorithm 170 for providing operator feedback upon occurrence of a high impedance condition in accordance with an embodiment of the present technology. In the depicted embodiment, the algorithm 170 evaluates data from the treatment and determines if detection of a high impedance event (block 172) was likely to involve a situation in which (a) tissue temperature was high and desiccation was likely, (b) the electrode moved, or (c) there was poor electrode contact or no electrode contact with the vessel wall. The algorithm 170 evaluates the data to determine which, if any, of these three situations occurred and displays one of three messages 174, 176, or 178 accordingly.

In accordance with one embodiment of the algorithm 170, upon detection of a high impedance (block 172), the maximum average temperature during the treatment is evaluated (decision block 180). If this temperature is above a certain threshold (e.g., at or above 60° C.) then the high impedance may be attributed to high tissue temperature resulting in desiccation. In this event, message 174 may be displayed instructing the clinician to check for a constriction or protrusion (i.e., to image the treatment site) and to avoid treating again in the same location. Conversely, if the temperature is below the threshold (e.g., below 60° C.), the algorithm 170 proceeds to decision block 182.

In the depicted embodiment, at decision block 182, the algorithm 170 evaluates if the high impedance event occurred early in treatment (e.g., in the first 20 seconds of energy delivery) when power is relatively low. If yes, it is unlikely that tissue temperature was high and more likely that the electrode initially had poor or no contact and subsequently established better contact, causing impedance to jump. In this event message 176 may be displayed instructing the clinician to attempt to establish better contact and repeat treatment at the same site. However, if the event occurs later in treatment (e.g., more than 20 seconds elapsed), the algorithm 170 proceeds to decision block 184.

At decision block 184, the algorithm 170 evaluates when the high impedance event occurred during treatment. For example, if the event occurred after a predetermined period of time (e.g., 45 seconds), when the power has reached high levels, the algorithm proceeds to decision block 186. However, if the event occurred when power is being ramped up and is not at its highest (e.g., between 20 seconds and 45 seconds), the algorithm proceeds to decision block 188.

At decision block 186, the algorithm 170 calculates the percentage change in impedance (% $\Delta Z$) at the time of the high impedance event compared to the impedance at a specified time (e.g., 45 seconds). This is the period when power is sustained at a high level. In one embodiment, the percentage change in impedance is calculated as:

$$\% \, \Delta Z = 100 * \left| \frac{[(\text{final avg } Z) - (\text{avg } Z \, @ \, 45 \, \text{sec})]}{(\text{avg } Z \, @ \, 45 \, \text{sec})} \right| \quad (2)$$

If % ΔZ is greater than or equal to a predetermined amount (e.g., 7%) then it may be likely that tissue began to desiccate due to high temperature. In this event, message 174 may be displayed instructing the clinician to check for a constriction or protrusion (i.e., to image the treatment site) and to avoid treating again in the same location. Otherwise, tissue desiccation is less likely and it is more likely that the electrode moved to cause the high impedance event. In this event, message 178 may be displayed notifying the clinician that the electrode may have moved. In the event the electrode has moved or may have moved, it is unlikely that tissue temperature reached a high level. Accordingly, it is expected that treating in the same location can be done if there are no or limited other locations to perform another treatment.

At decision block 188, the algorithm 170 may determine whether a sudden instability occurred. If such instability was present, it is likely that the electrode moved. In this event, message 178 may be displayed notifying the clinician that the electrode may have moved. As discussed above, the clinician may exhibit caution and avoid treating the original location or the location to which the electrode moved or the clinician may opt to treat in the same location if no other sites or a limited number of sites are available for further treatment. Otherwise, if no sudden instability occurred, it is more likely that the electrode had poor contact. In this event, message 176 may be displayed instructing the clinician to attempt to establish better contact and that treating the same site is safe.

The same objective of detecting high impedance conditions can be achieved using alternate measurements and calculations. For example, in a further embodiment of the algorithm 170, temperature and impedance data is taken for a sample time interval (e.g., 20 seconds). At a shorter time interval (e.g., every 1.5 seconds), the standard deviation of the impedance and temperature data is calculated. A first standard temperature for an interval is calculated as the standard deviation of the temperature divided by the standard deviation of the temperature at the initial time interval. If the standard deviation of the impedance measurements is greater than or equal to a pre-determined value (e.g., 10 Ohms), and the first standard temperature is greater than a pre-determined threshold (e.g., 3), then the algorithm 170 can display message 176, indicating poor electrode contact. However, if the standard deviation of the impedance measurement is outside the acceptable range, but the first standard temperature is within the acceptable range, then message 178 will be displayed to alert the clinician that there is electrode instability.

In accordance with a further embodiment of the algorithm 170, the impedance of two or more electrodes 24 (e.g., positioned on the treatment region 22 of the catheter 12 of FIG. 1) can each provide an independent impedance reading. During delivery of the therapeutic assembly 22 to the treatment site (e.g., within the renal artery), the impedance readings of the electrodes 24 are typically different due to the anatomy of the vasculature, as the catheter 12 will conform to the path of least resistance, often bending at vasculature curves to only contact one wall of the renal artery. In some embodiments, once the therapeutic assembly 22 is in position for treatment, the therapeutic assembly 22 can be expanded circumferentially to contact the entire circumferential surface of a segment of the renal artery wall. This expansion can place multiple electrodes 24 in contact with the renal artery wall. As the therapeutic assembly 22 is expanded into the treatment configuration and the electrodes 24 make increased contact with the renal artery wall, the impedance values of the individual electrodes 24 can increase and/or approach the same value. With good, stable contact, fluctuations of impedance values also reduce as described above. The energy generator 26 can continually or continuously monitor the individual impedance values. The values can then be compared to determine when contact has been effectively made, as an indication of successful treatment. In further embodiments, a moving average of impedance can be compared to a pre-determined range of variability of impedance values with limits set to guide stability measures.

F. Feedback Related to Vasoconstriction

In further embodiments, the system 10 may generate a message related to the occurrence of vasoconstriction. In particular, while treatment is being delivered, blood vessels may contract to a less-than-optimal diameter. Constricted blood vessels can lead to reduced blood flow, increased treatment site temperatures, and increased blood pressure. Vasoconstriction can be measured by sampling the amplitude (the "envelope") of real-time temperature data. The current envelope can be compared to a previous envelope sample taken (e.g., 200 ms prior). If the difference between the current envelope and the previous time point envelope is less than a pre-determined value (e.g., less than –0.5° C., or, in other words, there is a less than a 0.5 degree reduction in the present envelope value compared to the envelope value at the previous time point), then measurements are taken at a future time point (e.g., in 5 seconds). If the difference in average temperature at the future time point and the current time point is more than a given temperature threshold (e.g., more than 1° C.), then an algorithm 800 may determine that an undesirably high level of constriction exists, and can cease/alter energy delivery. In such an event, the system 10 may generate a message indicating the high constriction condition. However, depending on the circumstances, different actions by the clinician may be appropriate.

Figure 8:
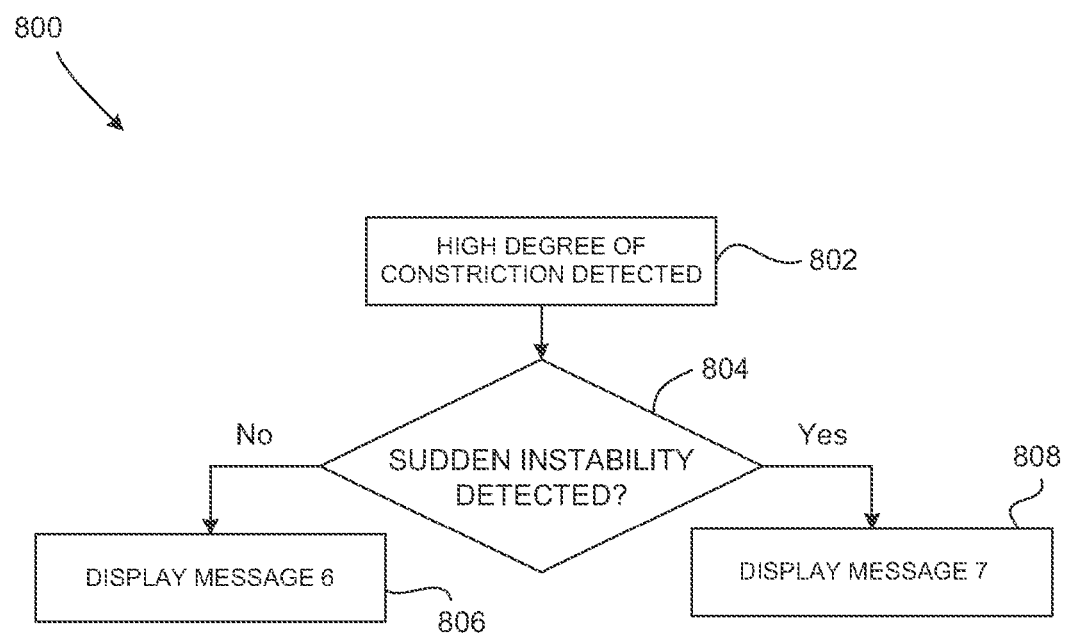
FIG. 8 is a block diagram illustrating an algorithm for providing operator feedback upon occurrence of a high degree of vessel constriction in accordance with an embodiment of the present technology.

FIG. 8, for example, is a block diagram illustrating an algorithm 800 for providing operator feedback when a high degree of vessel constriction is detected in accordance with an embodiment of the present technology. In one implementation, the algorithm 800 is executed in response to a high constriction level (e.g., vessels constricted at or below a certain diameter) (Block 802) and evaluates (decision block 804) data from the treatment to determine if the high constriction level involved a situation that included sudden instability or if it did not. An indication of sudden instability can indicate that the electrode 24 moved.

In the event that sudden instability is not detected at decision block 804, a first message may be displayed (block 806), such as an indication that a high constriction level has been detected and an instruction to a clinician to reduce treatment power. In further embodiments, the energy level may be automatically altered in response to the detected constriction level. In the event that sudden instability is detected at decision block 804, an alternative message may be displayed (block 808) that, in addition to indicating the occurrence of the high constriction level and instructions to the clinician, may also indicate the possibility that the electrode 24 may have moved from its original site. Such feedback may prompt the clinician to alter or cease treatment.

G. Feedback Related to Cardiac Factors

1. Feedback Related to Abnormal Heart Rate

Like other physiological conditions mentioned above, in certain circumstances the system 10 may generate a message related to the occurrence of an abnormal heart rate. In particular, while treatment is being delivered, heart rate may exceed or fall below desirable conditions (e.g., temporary procedural or chronic bradycardia). Instantaneous heart rate can be determined by measuring real-time temperature and impedance. More specifically, a real-time temperature reading can be filtered, for example, between 0.5 Hz and 2.5 Hz using a second order Butterworth filter. Local maxima of the filtered signal are determined. The local maxima are the detected peaks of the real-temperature signal. The instantaneous beat rate is the interval between the peaks, as the signal peaks correspond to the periodic change in the cardiac cycle.

In one implementation, the system 10 may cease/alter energy delivery if the heart rate falls outside a desirable range. In such an event, the system may generate a message indicating the adverse heart rate condition. However, depending on the circumstances, different actions by the clinician may be appropriate.

Figure 9A:
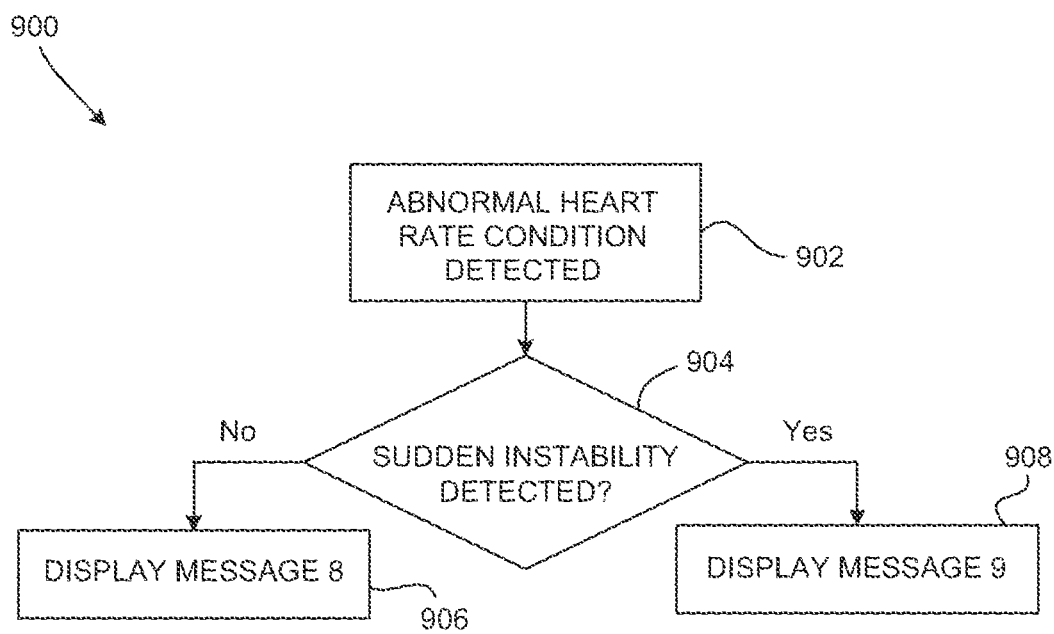
FIG. 9A is a block diagram illustrating an algorithm for providing operator feedback upon occurrence of an abnormal heart rate condition in accordance with an embodiment of the present technology.

FIG. 9A, for example, is a block diagram illustrating an algorithm 900 for providing operator feedback/instructions upon detection of an abnormal heart rate condition in accordance with an embodiment of the present technology. In one implementation, for example, the algorithm 900 may be executed in response to an abnormal heart rate condition (e.g., above or below a pre-determined threshold) (Block 902). At decision block 904, the algorithm 900 evaluates data from the treatment to determine if the detected abnormal heart rate condition involved a situation that included sudden instability. An indication of sudden instability can indicate that the electrode moved.

In the event that sudden instability is not detected at decision block 904, a first message may be displayed to the clinician (block 906), such as an indication that an abnormal heart rate has been detected and an instruction to the clinician to reduce treatment power. In further embodiments, the energy level may be automatically altered in response to the detected adverse heart rate. In the event that sudden instability is detected at decision block 904, an alternative message may be displayed (block 908) that, in addition to indicating the occurrence of the abnormal heart rate and instructions to the clinician, may also indicate the possibility that the electrode may have moved from its original site. Such feedback may prompt the clinician to alter or cease treatment.

2. Feedback Related to Low Blood Flow

The system 10 may also be configured to generate a message related to low blood flow conditions. For example, if blood flow falls below a certain level during treatment (or if vessels are undesirably narrow), the convective heat removed from the electrode 24 and tissue surface is reduced. Excessively high tissue temperatures can lead to the negative outcomes described above, such as thrombosis, charring, unreliable lesion size, etc. Reducing power from the generator 26 to prevent the tissue from reaching an unacceptable temperature can lead to insufficient lesion depth, and nerves may not be heated to sufficient ablation temperatures. An algorithm can be used to measure blood flow or the loss of heat to the blood stream. In one embodiment, blood flow can be measured with a flow meter or a Doppler sensor placed in the renal artery on a separate catheter or on the treatment catheter 12. In another embodiment, heat loss or thermal decay can be measured by delivering energy (e.g., RF energy) to raise a blood, tissue, or substrate temperature. The energy can be turned off and the algorithm can include monitoring the temperature as a gauge of thermal decay. A rapid thermal decay may represent sufficient blood flow, while a gradual thermal decay may represent low blood flow. For example, in one embodiment, the algorithm 910 can indicate a low blood flow if the slope of real-time temperature measurements over the starting temperature exceeds a preset threshold (e.g., 2.75) and the average temperature is greater than a preset temperature (e.g., 65° C.). In further embodiments, thermal decay and/or blood flow can be characterized by measuring temperature oscillations of an electrode delivering RF or resistive heat. At a given temperature or power delivery amplitude/magnitude, a narrow oscillation range may indicate a relatively low thermal decay/blood flow.

Figure 9B:
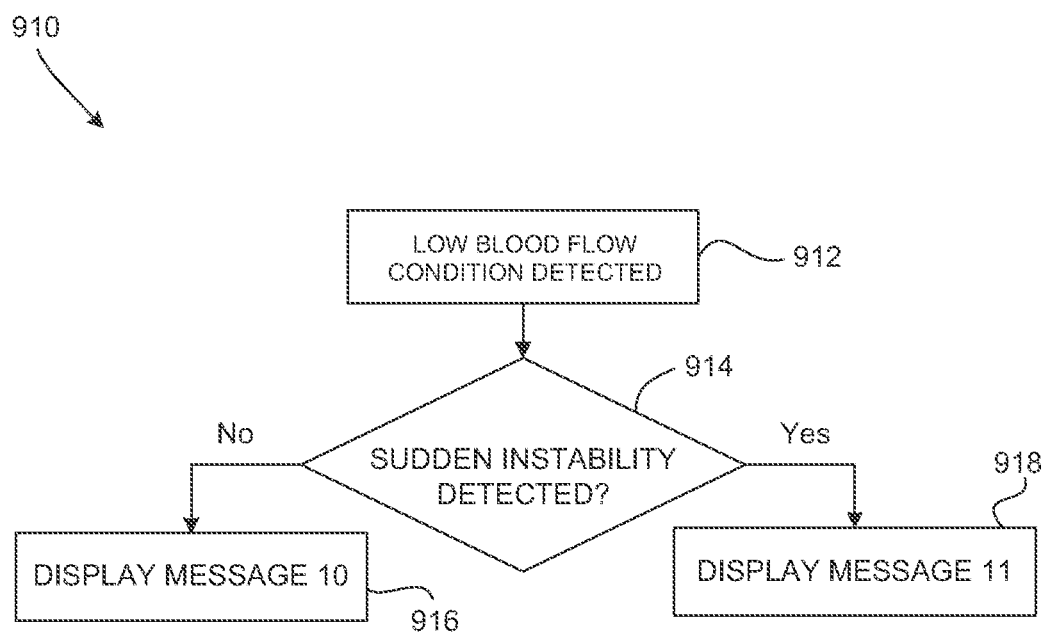
FIG. 9B is a block diagram illustrating an algorithm for providing operator feedback upon occurrence of a low blood flow condition in accordance with an embodiment of the present technology.

FIG. 9B, for example, is a block diagram illustrating an algorithm 910 for providing operator feedback/instructions upon occurrence of a low blood flow condition in accordance with an embodiment of the present technology. In one implementation, the algorithm 910 is executed in response to a detected low blood flow condition (e.g., flow below a pre-determined threshold) (Block 912). At block 914, the algorithm 910 evaluates data from the treatment to determine if the low blood flow condition involved a situation that included sudden instability. In the event that sudden instability is not detected at decision block 914, a first message may be displayed (block 916), such as an indication that low blood flow has been detected and an instruction to a clinician to reduce treatment power. In the event that sudden instability is detected, an alternative message may be displayed (block 918) that, in addition to indicating the occurrence of low blood flow and instructions to the clinician, may also indicate the possibility that the electrode may have moved from its original site. As noted above, such feedback may prompt the clinician to alter or cease treatment.

In further embodiments, if blood flow or thermal decay values are lower than a typical or pre-determined threshold, the energy delivery algorithm 910 can include automatically altering one or more conditions or characteristics of treatment or of the catheter to improve blood flow. For example, in one embodiment, the algorithm 910 can respond to a low blood flow by pulsing the energy provided to the energy delivery element 24 rather than providing continuous energy. This may allow the lower blood flow to more adequately remove heat from the tissue surface while still creating a sufficiently deep lesion to ablate a nerve.

In another embodiment, the algorithm 910 can include responding to a low blood flow by cooling the electrodes, as described in further detail in International Patent Application No. PCT/US2011/033491, filed Apr. 26, 2011, and U.S. patent application Ser. No. 12/874,457, filed Aug. 30, 2010. The foregoing applications are incorporated herein by reference in their entireties.

In a further embodiment, the algorithm 910 can respond to a low blood flow by requiring a manual increase of blood flow to the region. For example, a non-occlusive balloon can be inflated in the abdominal aorta, thereby increasing pressure and flow in the renal artery. The balloon can be incorporated on the treatment catheter or on a separate catheter.

H. Feedback Display

Figure 10A:
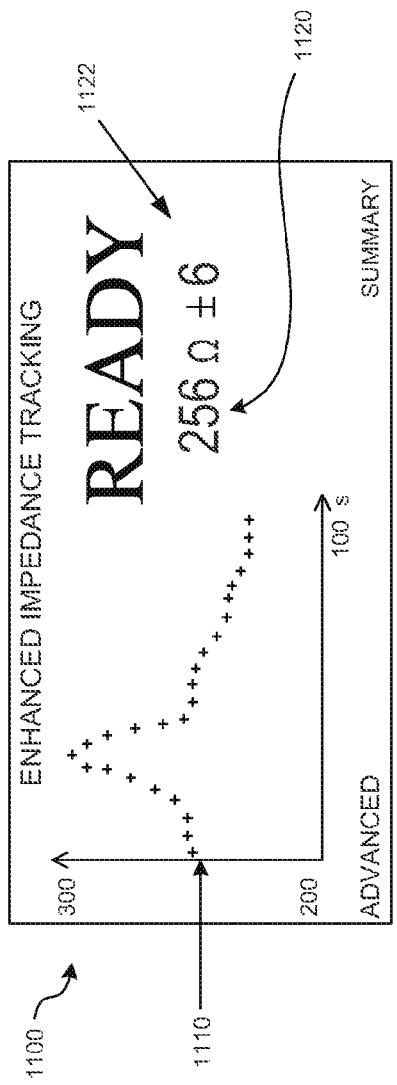
FIGS. 10A and 10B are screen shots illustrating representative generator display screens configured in accordance with aspects of the present technology.
Figure 10B:
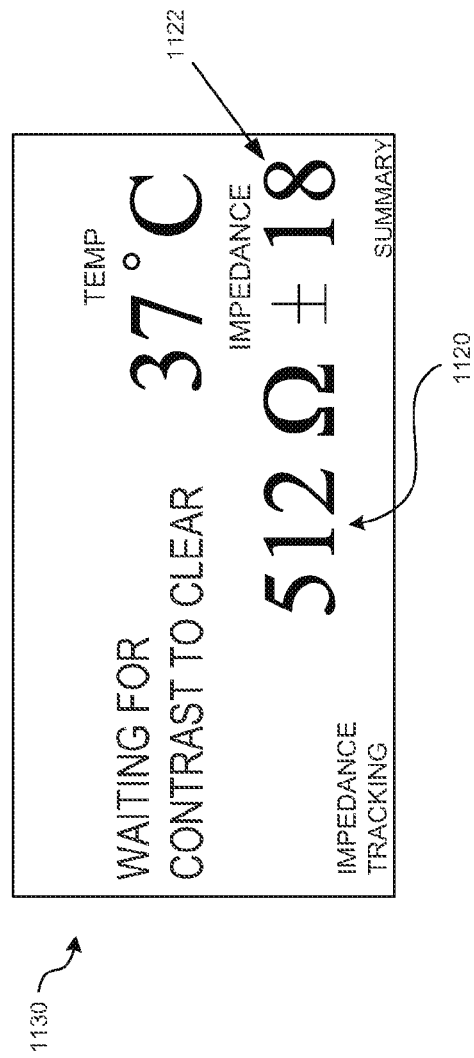

FIGS. 10A and 10B are screen shots illustrating representative generator display screens configured in accordance with aspects of the present technology. FIG. 10A, for example, is a display screen 1100 for enhanced impedance tracking during treatment. The display 1100 includes a graphical display 1110 that tracks impedance measurements in real time over a selected period of time (e.g., 100 seconds). This graphical display 1110, for example, can be a dynamic, rolling display that is updated at periodic intervals to provide an operator with both instantaneous and historical tracking of impedance measurements. The display 1110 can also includes an impedance display 1120 with the current impedance as well as a standard deviation indication 1122 for the impedance. In one embodiment, the standard deviation indication 1122 is configured to flash when this value is greater than 10. Such an indication can alert the operator of a contrast injection that is affecting the measurement or that the electrode may be unstable. Further information about contrast injection indications are described below.

FIG. 10B, for example, is another representative display screen 1130 with additional information for an operator. In this example, the display screen 1130 is configured to alert the operator of a contrast injection and that the system is waiting for contrast to clear before commencing (e.g., disable RF for approximately 1 to 2 seconds until contrast clears). In another embodiment, the display screen 1130 may be configured to provide other alert messages (e.g., "POSSIBLE UNSTABLE ELECTRODE," etc.). The additional information provided in the display screens 1110 and 1130 described above is expected to improve contact assessment prior to RF ON, and improve treatment efficiency and efficacy.

The additional information described above with reference to FIGS. 10A and 10B can be generated based on the algorithms described herein, or other suitable algorithms. In one embodiment, for example, an algorithm can continuously check for contrast injection/stability during pre-RF ON. If the electrode is stable and there is no contrast for ≥1 second, the baseline impedance Z is set equal to the average impedance Z over 1 second. In one particular example, the real time impedance is compared with two standard deviations of the mean impedance value within a one second window. In another specific example, the real time impedance may be compared with a fixed number (e.g., determine if the standard deviation is greater than 10). In still other examples, other arrangements may be used.

If the real time impedance measurement is within this range, no message is displayed. However, if the real time impedance is not within two standard deviations of the mean, the electrode may not stable (i.e., drifting, moving, etc.) and one or both of the message(s) described above with reference to FIGS. 10A and 10B may be displayed to the user (e.g., "WAITING FOR CONTRAST TO CLEAR," "POSSIBLE UNSTABLE ELECTRODE"). By way of example, for contrast injection detection, in addition to the standard deviation of the impedance, the algorithm may be configured to factor in the standard deviation of a real time temperature measurement to look for excursions of the real time temperature below a starting body temperature. The exact value for the temperature excursion cut off can vary. In one particular example, the system is configured such that if there is an increase in impedance (e.g., standard deviation>10) accompanied by a drop in real time temperature, the system will flag a Contrast Detected event leading to the "WAITING FOR CONTRAST TO CLEAR" message to be displayed to the operator. In other examples, however, other algorithms and/or ranges may be used to determine contrast injection events and/or the stability of the electrode. Further, in some embodiments the system may modify/adjust various treatment parameters based on detected conditions without displaying such messages to the clinician.

IV. Pertinent Anatomy and Physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal denervation. For example, as mentioned previously, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympathoadrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 11:
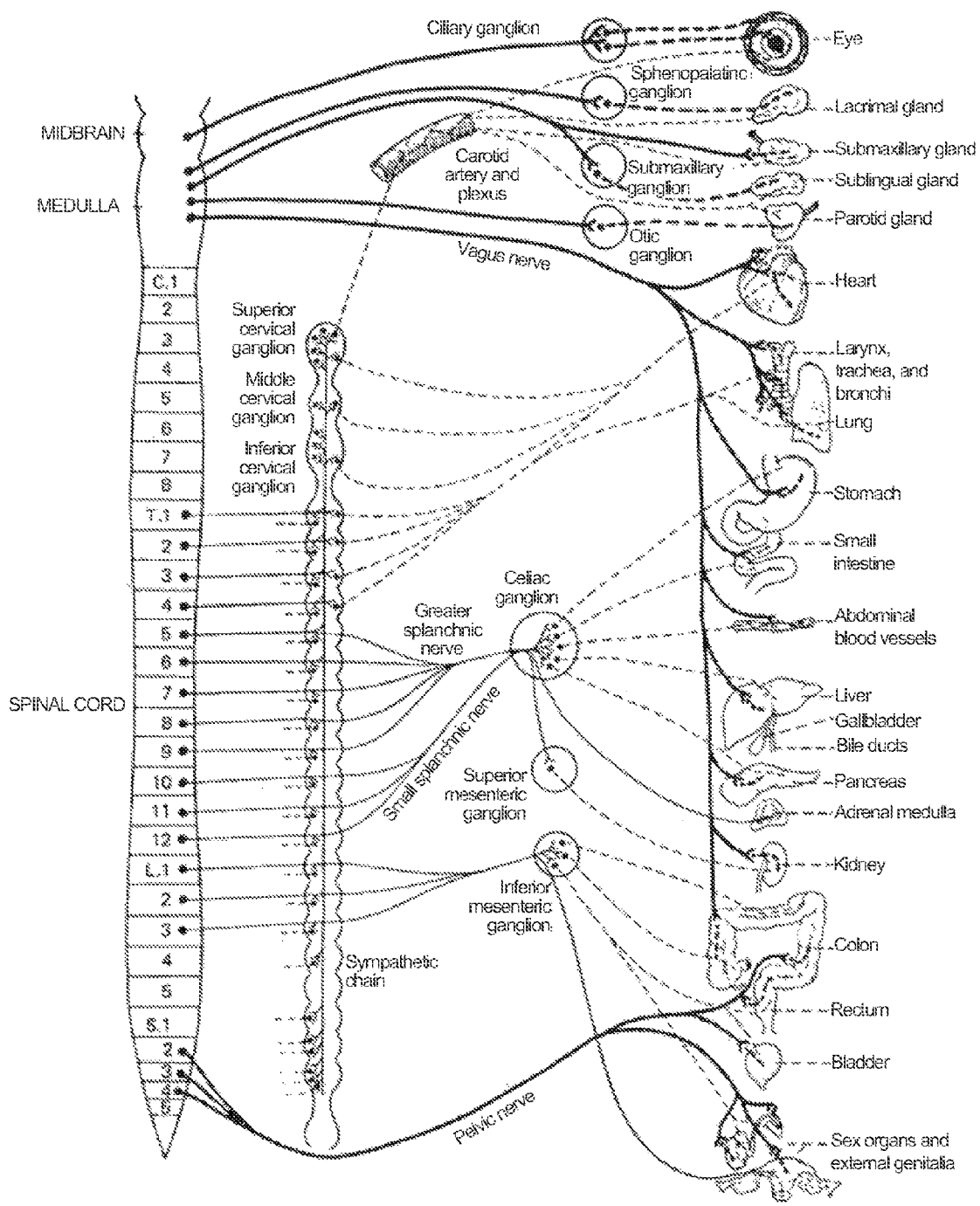
FIG. 11 is a conceptual illustration of the sympathetic nervous system (SNS) and how the brain communicates with the body via the SNS.

As shown in FIG. 11, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 12:
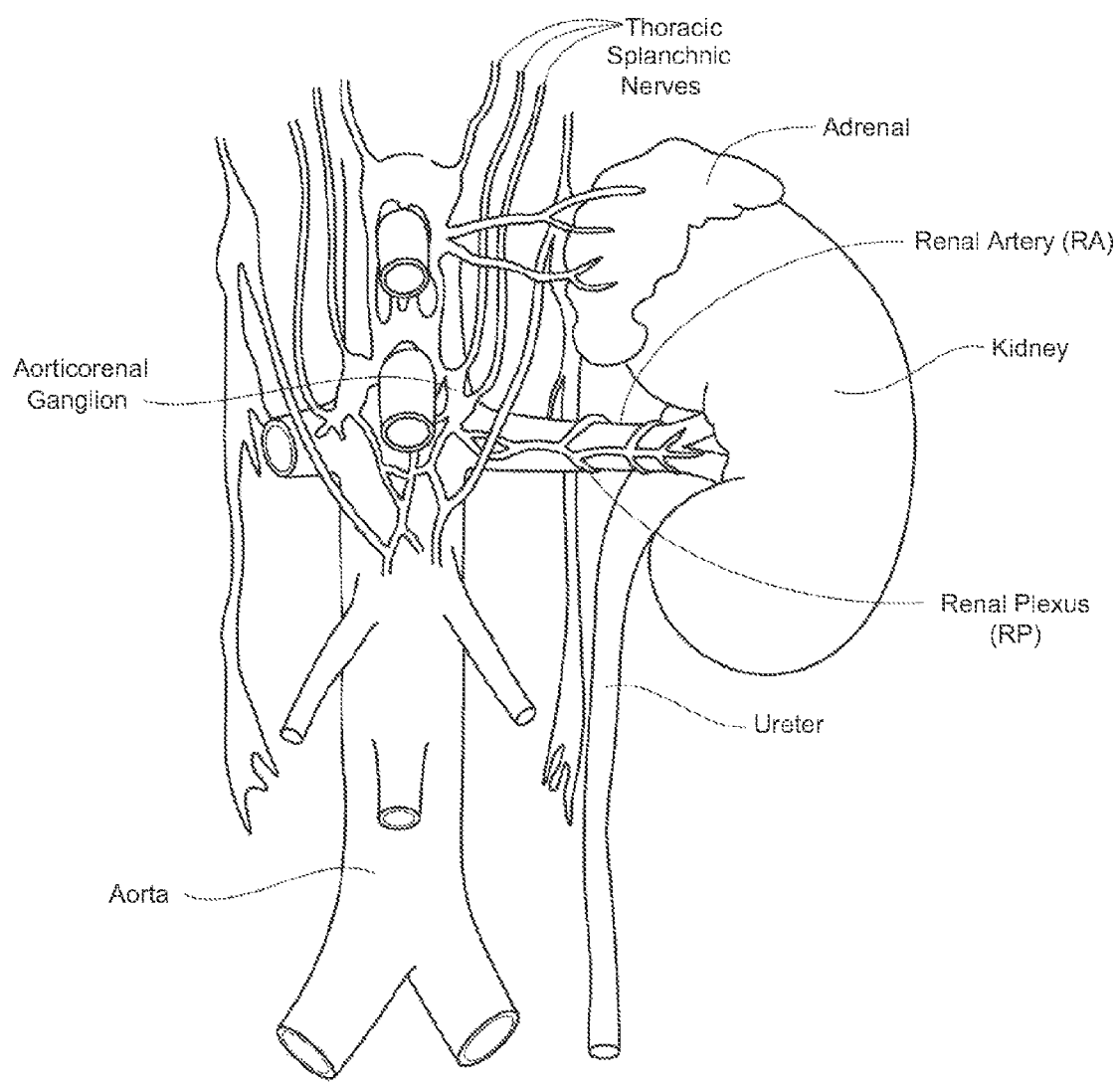
FIG. 12 is an enlarged anatomic view of nerves innervating a left kidney to form the renal plexus surrounding the left renal artery.

As FIG. 12 shows, the kidney is innervated by the renal plexus RP, which is intimately associated with the renal artery. The renal plexus RP is an autonomic plexus that surrounds the renal artery and is embedded within the adventitia of the renal artery. The renal plexus RP extends along the renal artery until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules.

Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 13A:
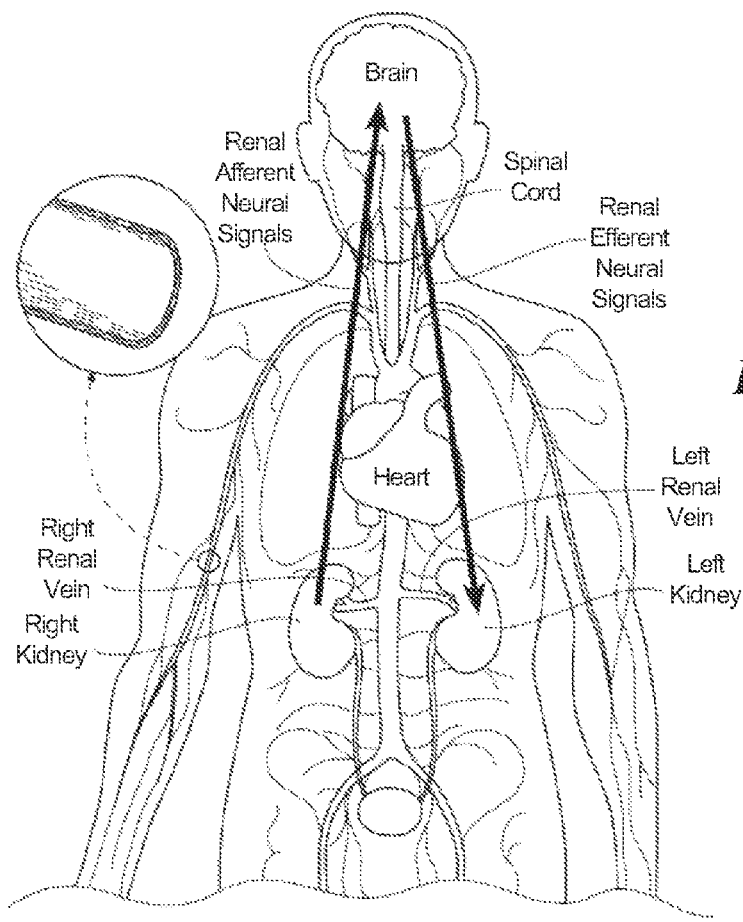
FIGS. 13A and 13B provide anatomic and conceptual views of a human body, respectively, depicting neural efferent and afferent communication between the brain and kidneys.
Figure 13B:
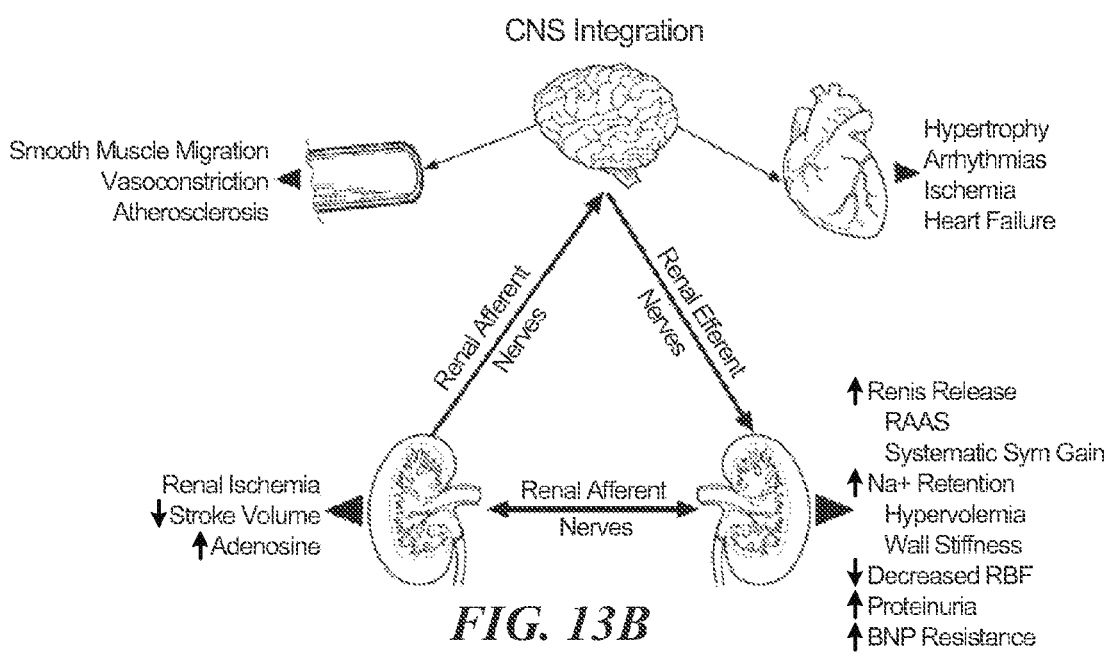

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 13A and 13B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 11. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figures 14A, 14B:
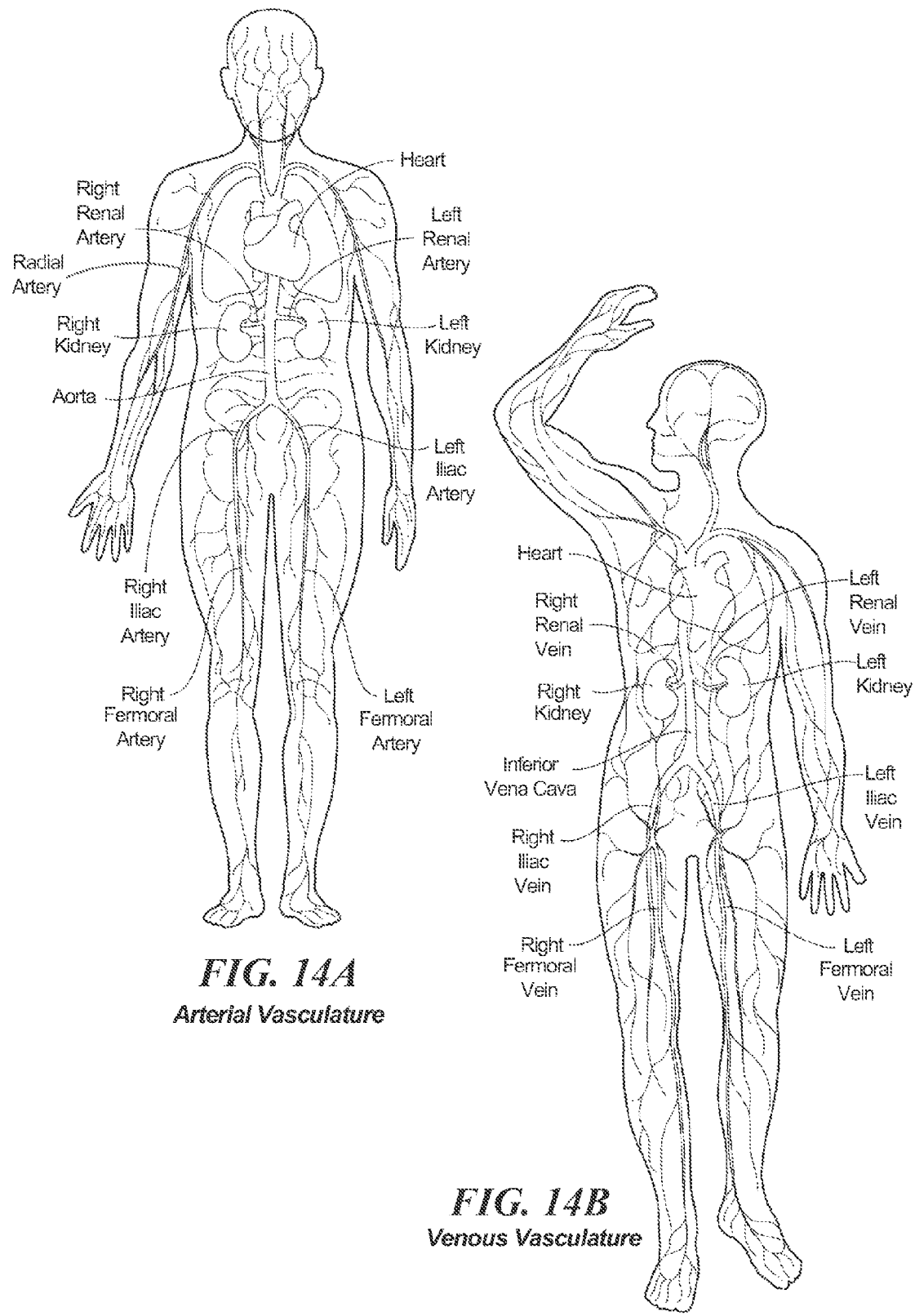
FIGS. 14A and 14B are, respectively, anatomic views of the arterial and venous vasculatures of a human.

In accordance with the present technology, neuromodulation of a left and/or right renal plexus RP, which is intimately associated with a left and/or right renal artery, may be achieved through intravascular access. As FIG. 14A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 14B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus RP may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, consistent positioning and appropriate contact force applied by the energy delivery element to the vessel wall are important for predictability. However, navigation is impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e., cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the mesh structures described herein and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility: and (f) as well as the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta, induced by respiration and/or blood flow pulsatility. A patient's kidney, which located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

V. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively. For example, as noted previously, although much of the disclosure herein describes an energy delivery element 24 (e.g., an electrode) in the singular, it should be understood that this disclosure does not exclude two or more energy delivery elements or electrodes.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for evaluation and feedback of a neuromodulation treatment, the method comprising:
    placing a first energy delivery element carried by an intravascular catheter at a treatment site within a renal blood vessel of a human patient;
    increasing energy delivery to the first energy delivery element, wherein energy delivery is increased to a predetermined first power level over a first period of time, and wherein the first energy delivery element is positioned to deliver energy to target neural fibers proximate to a wall of the renal blood vessel;
    maintaining energy delivery at the first power level for a second period of time;
    increasing energy delivery to a second predetermined power level if the temperature value is less than a preset threshold temperature following the second period of time;
    obtaining a set of treatment data corresponding to a completed treatment performed using the first energy delivery element;
    evaluating the set of treatment data in view of one or more criteria to determine if a valuation of the completed treatment is within a pre-determined range; and
    providing an indication as to whether the valuation of the completed treatment is within the pre-determined range.

2. The method of claim 1 wherein obtaining a set of treatment data comprises measuring from within or adjacent to the first energy delivery element one or more of temperature, impedance, blood flow, or movement of the first energy delivery element.

3. The method of claim 1 wherein obtaining a set of treatment data comprises measuring one or more of temperature, time, impedance, power, blood flow, blood flow velocity, volumetric blood flow rate, blood pressure, or heart rate.

4. The method of claim 1 wherein obtaining a set of treatment data comprises taking one or more measurements related to a change in temperature over a specified time, a maximum temperature, a maximum average temperature, a minimum temperature, a temperature at a predetermined or calculated time relative to a predetermined or calculated temperature, an average temperature over a specified time, a maximum blood flow, a minimum blood flow, a blood flow at a predetermined or calculated time relative to a predetermined or calculated blood flow, an average blood flow over time, a maximum impedance, a minimum impedance, an impedance at a predetermined or calculated time relative to a predetermined or calculated impedance, a change in impedance over a specified time, or a change in impedance relative to a change in temperature over a specified time.

5. The method of claim 1 wherein obtaining the set of treatment data comprises obtaining a first set of treatment data corresponding to a first completed treatment, and wherein the method further comprises:
    modifying the first predetermined power level, the first period of time, the second period of time, and/or the second predetermined power level based, at least in part, on the evaluation of the first treatment data and the indication as to whether the valuation of the first completed treatment is within the pre-determined range;
    performing a second treatment using the modified first predetermined power level, modified first period of time, modified second period of time, and/or modified second predetermined power level; and obtaining a second set of treatment data corresponding to a second completed treatment.

6. The method of claim 1 wherein evaluating the set of treatment data comprises generating a score and using the score to determine whether the completed treatment was within the pre-determined range or if the completed treatment did not proceed as expected.

7. The method of claim 1 wherein evaluating the set of treatment data comprises performing a linear discriminant analysis.

8. The method of claim 7 wherein the linear discriminant analysis generates a score and wherein evaluating the set of treatment data uses the score to determine whether the completed treatment was within the pre-determined range.

9. The method of claim 1 wherein providing an indication comprises displaying a message on a display screen of a system used to administer the completed treatment.

10. The method of claim 9 wherein providing an indication as to whether the completed treatment was within the pre-determined range comprises:

displaying a first message on the display screen if the valuation of the treatment is within the pre-determined range; and displaying a second, different message on the display screen if the valuation of the treatment indicated that treatment did not proceed as expected.

11. The method of claim 1 wherein increasing energy delivery to a predetermined second power level if an operating parameter is outside a pre-determined range comprises increasing energy delivery to a pre-determined second power level if a difference in impedance values from either or both the first energy delivery element and a second energy delivery element is outside a pre-determined range.

12. The method of claim 1 wherein the first energy delivery element comprises an electrode.

13. The method of claim 1 wherein the intravascular catheter comprises a plurality of energy delivery elements.

14. The method of claim 13 wherein the plurality of energy delivery elements comprise a plurality of electrodes.

15. The method of claim 14 wherein the renal blood vessel comprises a renal artery.

16. The method of claim 1 wherein the renal blood vessel comprises a renal artery.

17. The method of claim 16, further comprising ablating the target neural fibers.

18. The method of claim 1, further comprising ablating the target neural fibers.

* * * * *